(12) United States Patent
Kelly et al.

(10) Patent No.: US 11,931,522 B2
(45) Date of Patent: Mar. 19, 2024

(54) INFLATION LUMEN KINK PROTECTION AND BALLOON PROFILE

(71) Applicant: Neuravi Limited, Galway (IE)

(72) Inventors: Ronald Kelly, Galway (IE); Michael Gilvarry, Galway (IE); David Vale, Galway (IE); Brendan Casey, Galway (IE); Maeve Holian, Galway (IE); Denis Foley, Galway (IE)

(73) Assignee: NEURAVI LIMITED, Galway (IE)

(*) Notice: Subject to any disclaimer, the term of this patent is extended or adjusted under 35 U.S.C. 154(b) by 923 days.

(21) Appl. No.: 16/601,185

(22) Filed: Oct. 14, 2019

(65) Prior Publication Data

US 2020/0353205 A1 Nov. 12, 2020

Related U.S. Application Data

(60) Provisional application No. 62/845,683, filed on May 9, 2019, provisional application No. 62/845,699, filed
(Continued)

(51) Int. Cl.
*A61B 17/12* (2006.01)
*A61M 25/00* (2006.01)
(Continued)

(52) U.S. Cl.
CPC ..... *A61M 25/005* (2013.01); *A61B 17/12109* (2013.01); *A61B 17/12136* (2013.01);
(Continued)

(58) Field of Classification Search
CPC ........ A61M 25/005; A61M 2025/1061; A61M 2025/1084; A61M 25/0026;
(Continued)

(56) References Cited

U.S. PATENT DOCUMENTS

| 4,323,071 A | 4/1982 | Simpson et al. |
| 4,684,363 A | 8/1987 | Ari et al. |

(Continued)

FOREIGN PATENT DOCUMENTS

| JP | 2016168151 | 9/2016 |
| WO | 2007139799 | 12/2007 |

(Continued)

OTHER PUBLICATIONS

Co-Pending, co-owned, U.S. Appl. No. 16/601,256, filed Oct. 14, 2019.
(Continued)

*Primary Examiner* — Darwin P Erezo
*Assistant Examiner* — Mitchell Brian Hoag
(74) *Attorney, Agent, or Firm* — TROUTMAN PEPPER HAMILTON SANDERS LLP

(57) ABSTRACT

A balloon guide catheter having a sleeved inflation lumen secured with a wire wrap for improved inflation lumen kink protection and a welded balloon construction provides a robust and flexible catheter with an exceptionally large inner lumen relative to its outer profile and enables rapid and reliable balloon inflation and deflation in a highly deliverable and kink resistant catheter. Balloon guide catheters having multiple sleeved inflation lumens and proximal luers for utilizing the multiple inflation lumens are also provided.

24 Claims, 27 Drawing Sheets

Related U.S. Application Data on May 9, 2019, provisional application No. 62/845,747, filed on May 9, 2019, provisional application No. 62/845,711, filed on May 9, 2019.

(51) Int. Cl.
*A61M 25/10* (2013.01)
*A61M 39/22* (2006.01)

(52) U.S. Cl.
CPC .... *A61M 25/0032* (2013.01); *A61M 25/0097* (2013.01); *A61M 25/1002* (2013.01); *A61M 25/10185* (2013.11); *A61M 39/223* (2013.01); *A61M 2025/0039* (2013.01); *A61M 2025/0059* (2013.01); *A61M 2025/1061* (2013.01)

(58) Field of Classification Search
CPC .. A61M 2025/0059; A61M 2025/0039; A61M 25/1002; A61M 25/0032; A61B 2017/22048
See application file for complete search history.

(56) References Cited

U.S. PATENT DOCUMENTS

| | | | |
|---|---|---|---|
| 4,715,378 A | 12/1987 | Pope, Jr. et al. | |
| 4,753,238 A | 6/1988 | Gaiser | |
| 4,793,351 A | 12/1988 | Landman et al. | |
| 4,811,737 A | 3/1989 | Rydell | |
| 4,821,722 A | 4/1989 | Miller et al. | |
| 5,035,705 A | 7/1991 | Burns | |
| 5,100,385 A | 3/1992 | Bromander | |
| 5,135,486 A | 8/1992 | Eberle et al. | |
| 5,176,698 A | 1/1993 | Burns et al. | |
| 5,224,933 A | 7/1993 | Bromander | |
| 5,256,143 A | 10/1993 | Miller et al. | |
| 5,800,421 A | 9/1998 | Lemelson | |
| 6,102,891 A | 8/2000 | Maria van Erp | |
| 6,102,931 A | 8/2000 | Thornton | |
| 6,709,429 B1 * | 3/2004 | Schaefer | D04C 1/06 604/524 |
| 6,811,559 B2 | 11/2004 | Thornton | |
| 6,953,431 B2 * | 10/2005 | Barthel | A61B 1/00096 600/116 |
| 6,994,687 B1 | 2/2006 | Shkolnik | |
| 7,160,266 B2 | 1/2007 | Shkolnik | |
| 7,338,511 B2 | 3/2008 | Mirigian et al. | |
| 7,678,075 B2 * | 3/2010 | Wantink | A61M 25/10 604/96.01 |
| 8,298,218 B2 | 10/2012 | Mahrouche | |
| 8,926,560 B2 | 1/2015 | Dinh et al. | |
| 9,155,869 B2 | 10/2015 | Ehrenreich et al. | |
| 9,463,035 B1 | 10/2016 | Greenhalgh et al. | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign et al. | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman et al. | |
| 9,770,577 B2 | 9/2017 | Li et al. | |
| 9,775,621 B2 | 10/2017 | Tompkins et al. | |
| 9,775,706 B2 | 10/2017 | Peterson et al. | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman et al. | |
| 9,833,252 B2 | 12/2017 | Sepetka et al. | |
| 9,833,604 B2 | 12/2017 | Lam et al. | |
| 9,833,625 B2 | 12/2017 | Waldhauser et al. | |
| 10,576,254 B2 * | 3/2020 | Yang | A61M 25/1029 |
| 10,682,152 B2 | 6/2020 | Vale et al. | |
| 11,202,891 B2 * | 12/2021 | Gulachenski | A61M 25/10185 |
| 2002/0103473 A1 | 8/2002 | Roychowdhury et al. | |
| 2003/0023204 A1 * | 1/2003 | Vo | A61F 2/014 604/916 |
| 2004/0260329 A1 * | 12/2004 | Gribbons | A61M 25/09041 977/902 |
| 2005/0070881 A1 * | 3/2005 | Gribbons | A61M 25/0052 604/525 |
| 2005/0124932 A1 | 6/2005 | Foster et al. | |
| 2005/0182359 A1 | 8/2005 | Chin et al. | |
| 2006/0030814 A1 * | 2/2006 | Valencia | A61M 25/00 604/93.01 |
| 2008/0200904 A1 | 8/2008 | Cluff et al. | |
| 2010/0234940 A1 * | 9/2010 | Dolan | A61F 2/2436 623/2.11 |
| 2012/0265134 A1 * | 10/2012 | Echarri | A61M 25/005 604/525 |
| 2012/0296366 A1 * | 11/2012 | Rundquist | A61M 25/1027 219/121.64 |
| 2013/0289549 A1 | 10/2013 | Nash et al. | |
| 2014/0188043 A1 | 7/2014 | Shibahara | |
| 2014/0257359 A1 * | 9/2014 | Tegels | A61B 17/0057 606/194 |
| 2015/0032049 A1 * | 1/2015 | Hopkinson | A61M 25/10 604/103.09 |
| 2015/0073467 A1 * | 3/2015 | Eaton | A61M 25/10 606/194 |
| 2015/0174363 A1 * | 6/2015 | Sutermeister | A61M 25/005 604/95.04 |
| 2015/0224290 A1 | 8/2015 | Chanduszko et al. | |
| 2016/0001040 A1 * | 1/2016 | Yamaguchi | A61M 25/0053 604/95.04 |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu et al. | |
| 2017/0027640 A1 | 2/2017 | Kunis et al. | |
| 2017/0027692 A1 | 2/2017 | Bonhoeffer et al. | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042548 A1 | 2/2017 | Lam | |
| 2017/0049596 A1 | 2/2017 | Schabert | |
| 2017/0071737 A1 | 3/2017 | Kelley | |
| 2017/0072452 A1 | 3/2017 | Monetti et al. | |

(56) References Cited

U.S. PATENT DOCUMENTS

| | | |
|---|---|---|
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0333192 A1 | 11/2018 | Sliwa et al. |
| 2019/0167287 A1 | 6/2019 | Vale et al. |
| 2019/0359786 A1 | 11/2019 | Trahan et al. |
| 2020/0179657 A1* | 6/2020 | Liu .................. A61M 25/0012 |
| 2020/0246036 A1* | 8/2020 | Kallmes ............ A61B 17/3207 |
| 2020/0353226 A1* | 11/2020 | Keating ........... A61B 17/12136 |
| 2022/0143360 A1* | 5/2022 | Kugler ................ A61M 25/005 |

FOREIGN PATENT DOCUMENTS

| | | |
|---|---|---|
| WO | 2013163254 | 10/2013 |
| WO | 2017192999 | 11/2017 |

OTHER PUBLICATIONS

Co-Pending, co-owned, U.S. Appl. No. 16/601,221, filed Oct. 14, 2019.

Co-Pending, co-owned, U.S. Appl. No. 16/601,202, filed Oct. 14, 2019.

L.E. Romans, "The Use of Contrast Media in the CT Department", CEWebsource.com, May 15, 2013 (50 pp).

* cited by examiner

Section B-B

Section C-C

Section B-B

Section C-C

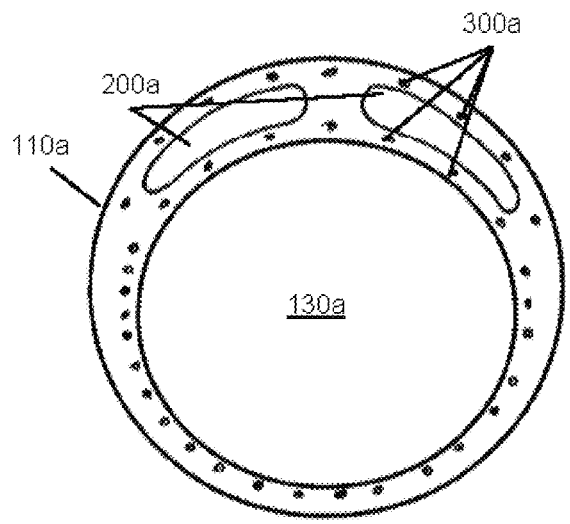 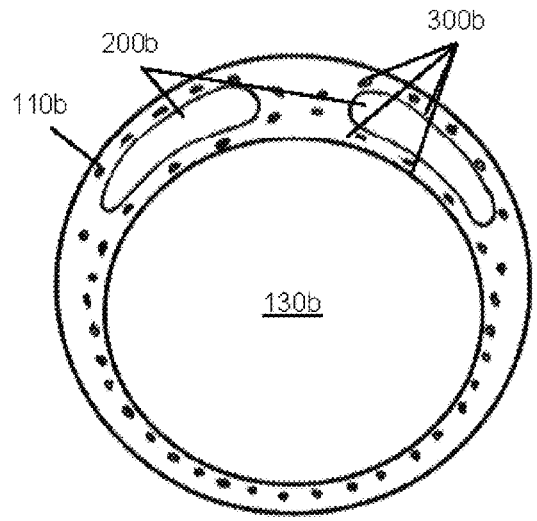
FIG. 16A  FIG. 16B
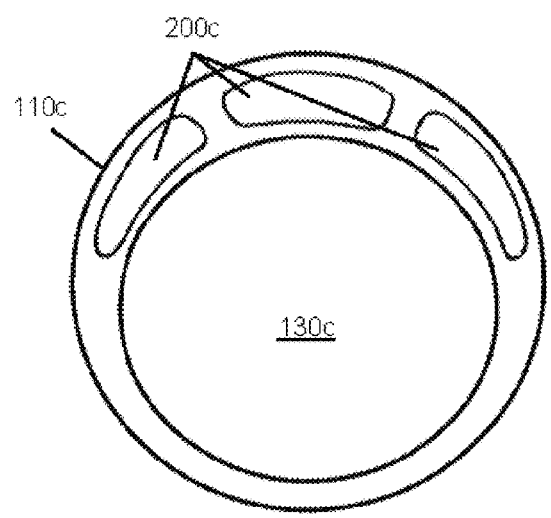 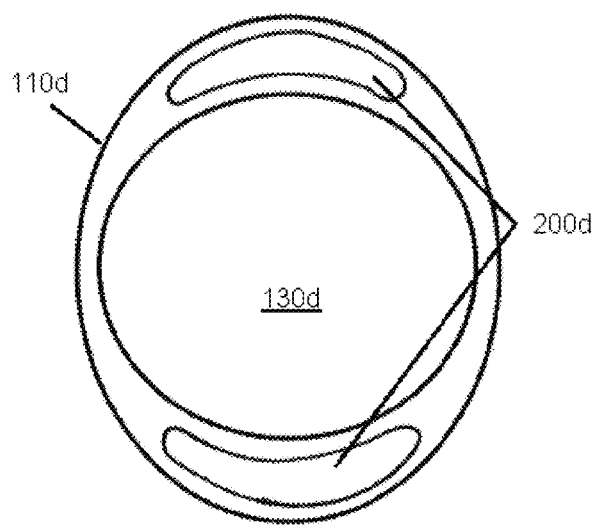
FIG. 16C  FIG. 16D

INFLATION LUMEN KINK PROTECTION AND BALLOON PROFILE

CROSS-REFERENCE TO RELATED APPLICATIONS

This application claims the benefit of the following: U.S. Provisional Application No. 62/845,683, filed on May 9, 2019; U.S. Provisional Application No. 62/845,699, filed on May 9, 2019; U.S. Provisional Application No. 62/845,711, filed on May 9, 2019; and U.S. Provisional Application No. 62/845,747, filed on May 9, 2019, each of which is herein incorporated by reference in its entirety.

FIELD OF INVENTION

The present invention generally relates to medical instruments, and more particularly, to balloon devices for occluding blood vessels during vascular surgery.

BACKGROUND

Catheters can be pliable tubular structures that enter the vasculature of a patient. Catheters can be used for a variety of purposes and applications. For example, they can be introduced into a particular area of interest within a vasculature and then act as a guide for introducing other peripheral, central venous, or arterial devices therein through its lumen. Such devices can include single or multi-lumen catheters, clot capturing devices, balloon catheters, and the like.

Balloon guide catheters can be used in ischemic stroke procedures to act as a conduit for diagnostic and therapeutic devices and also to provide flow arrest and/or flow control and/or flow reversal to aid in the safe retrieval of a clot from the patient. These balloon guide catheters must be sufficiently flexible to be delivered through tortuous vasculature to the target site (typically the Internal Carotid Artery of a patient if used in the anterior vasculature) and sufficiently robust to remain stable in that position while other devices are advanced, manipulated and withdrawn through the catheter. It is desirable for balloon guide catheters used in such applications to have as large an internal lumen as possible in order that the largest possible therapeutic catheters (such as intermediate or aspiration catheters) can be advanced through them, and to maximize the distal opening size for the safe retrieval of clot. It is also desirable for any guides or sheaths used to have as small an outer diameter as possible to minimize trauma to the patient and minimize the size of the entry orifice that must be closed once the catheters are removed from the patient.

Therefore, there remains a need for new devices to deal with these conflicting requirements and provide a large lumen, low profile, and flexible balloon guide.

SUMMARY

This invention facilitates the installation of a catheter into the Internal Carotid Artery to serve as a conduit for devices, as well as securing the catheter, arresting blood flow, and generating improved aspiration efficacy when aspirating the main central lumen of the catheter. This invention accomplishes such objectives through the increased flexibility of the distal end of the catheter and through the shape and profile of a seamless balloon.

Procedures can involve placing a balloon guide catheter into the Internal Carotid Artery to serve as conduit for devices such as guidewire(s), microcatheter, stentriever or intermediate catheters. The installation of the guide catheter can protect the access vessels and shorten procedural times. The balloon can secure the balloon guide catheter approximate a treatment site, arrest blood flow, and generate improved aspiration efficacy when aspirating the main central lumen of the balloon guide catheter and/or when aspirating through an intermediate catheter and/or when manipulating a stentriever or other thrombectomy device. Depending on the vessel tortuosity, a balloon guide catheter can be exposed to extreme angulations presented by the vessels as well as carotid artery loops and syphon-like geometries. Tortuosity can induce forces on the catheter and the inflation lumen. In some instances, extreme angulations and/or force can cause a "kink" or "kinking" within the inflation lumen.

A kinked inflation lumen can inhibit flow to and from the balloon of the balloon guide catheter, which can reduce the rate of inflation or deflation of the balloon. In some cases, a kinked inflation lumen can result in the complete failure of the balloon or complete inability to inflate or deflate the balloon. This can create complications during a treatment as the non-functioning balloon guide catheter may need to be removed, a physician may need to conduct a procedure without blood-flow arrest, or a mandrel may need to be inserted through the inflation lumen to deflate the balloon.

It has also been observed during testing that when thrombectomy devices are retrieved into balloon catheters, soft clots can shear off the thrombectomy device and remain on the catheter tip (proximal to the tip and distal to the balloon). This can occur when there is dead space between the balloon and the distal end of the catheter. On deflation of the balloon, these fragments may travel distally and result in embolization of distal vessels—potentially resulting in additional procedural time or impact to patient health.

To address the deficiencies in the existing art, the disclosed invention incorporates a reinforcing wire configuration within the catheter and alters the balloon profile and/or shape. The wire configuration can be braided over and below the inflation lumen thereby reinforcing the catheter and elongated tubular member. The disclosed invention also incorporates tie-layers, welds, and bonds to facilitate the balloon shape and profile. The disclosed invention can increase the flexibility of the distal end of the catheter while minimizing the likelihood of kinking through the wire configuration design and balloon profile and/or shape.

Disclosed herein are various exemplary devices for inflation lumen kink protection and balloon profile that can address tracking of catheter through tortuous anatomy and maximizing clot removal and other problems of the art.

The devices can generally include an elongated tubular member and a balloon.

The elongated tubular member can have a proximal end, a distal end, an outer surface, a top, and a bottom. The elongated tubular member having an inner hollow lumen, an inner core, and an inflation lumen. The inner hollow lumen can extend between the proximal end and distal end of the elongated tubular member. The inner lumen can be sized to maximize clot capture and can be indicated for use as a conduit for clot retrieval devices. The inner lumen can have an inner diameter of about 0.088". The inner core can extend between the proximal end and distal end of the elongated tubular member having an inner core thickness. The inflation lumen can extend between a port at the proximal end and the inside of the balloon at the distal end of the elongated tubular member. The elongated tubular member can have wires configured to secure the inflation lumen.

The inflation lumen can serve as a conduit for inflating and deflating the balloon. The inflation lumen can connect to a port at the proximal end of the catheter, extend a majority of the length of the elongated tubular member, and connect to the inside of the balloon. The inflation lumen can have any number of shapes, including but not limited to particular arc radius dimensions. The inflation lumen can be a sleeve of Polytetrafluoroethylene (PPTFE), Polyethylene (PE), Polyethylene terephthalate (PET), fluorinated ethylene propylene (FEP), and the like. The inflation lumen can be a crescent shape with a CSA of approximately or about 0.2 mm$^2$.

The elongated tubular member can include two inflation lumens. Each inflation lumen can serve as a conduit for inflating and deflating the balloon. The combination of the inflation lumens can serve as a contiguous path for flushing the balloon and inflation lumens with fluid such that fluid can enter one of the two inflation lumens and exit the other inflation lumen during flushing. The combination of inflation lumens can provide an additional flow path to expedite inflation and deflation of the balloon. The combination of inflation lumens can provide redundancy in flow path; in an instance where one of the inflation lumens becomes blocked, kinked, or otherwise compromised, the other of the inflation lumens can be used to inflate and deflate the balloon.

The elongated tubular member can include three inflation lumens. Each inflation lumen can serve as a conduit for inflating and deflating the balloon. The third lumen can provide the benefits of having two inflation lumens as described with an additional inflation lumen for additional redundancy.

The inflation lumen can have a cross sectional area, or the combination of multiple inflation lumens can collectively have a cross sectional area that is about 0.15 mm$^2$ to about 0.20 mm$^2$, about 0.20 mm$^2$ to about 0.25 mm$^2$, and/or about 0.25 mm$^2$ to about 0.30 mm$^2$. The total inflation lumen cross sectional area can be made up of more than one inflation lumen.

The elongated tubular member can include wires configured to secure the inflation lumen along at least a portion of or a majority of the length of the elongated tubular member. The wires can provide kink protection for the inflation lumen. The wire configuration can enhance the torque of the catheter and flexibility of the distal end of the catheter. The wire configuration can also contribute to the strength of the elongated tubular member while increasing the flexibility and reducing the overall stiffness of the catheter.

The elongate tubular member can be reinforced with a braided wire matrix in such a pattern that all of the wires running over the inflation lumen run substantially parallel to one other, and do not cross over each other in the region of the inflation lumen. The same is true for those wires running beneath the inflation lumen. They do cross over each other either side of the inflation lumen, but not above or below it. This minimizes the chance of the wires pinching and rupturing the inflation lumen, causing a leak.

The wire configuration can be a braid configuration that splits over and under the inflation lumen. The wire configuration can be a dual wire double diamond. When an elongated tubular member includes two inflation lumens, the wire configuration can be a dual wire double diamond wrapping both of the inflation lumens.

While the inflation lumen can increase the stiffness of the catheter compared to catheters that do not include an inflation lumen, the wire configuration can help lower the flexural stiffness of the catheter compared to known balloon guide catheters. Therefore, the wire configuration can lower the stiffness and/or increase the flexibility potentially offsetting the increased stiffness due to the inflation lumen, resulting in a balloon guide catheter with increased flexibility compared to known balloon guide catheters. The reduced stiffness and/or increased flexibility provided by the wire configuration can allow easier orientation during insertion of the device.

The elongated tubular member can have a uniform stiffness across its length, a stiffness that varies along the length of the elongated tubular member. To achieve a desired stiffness, materials and/or additives having desired stiffness properties can be used in the construction of the elongated tubular member. Materials and/or additives can be varied along the length of the elongated tubular member to create portions having differing stiffness, each portion being of a different stiffness or durometer. Additional layers or additives can be provided to control the individual stiffness. In some examples, the stiffness of the elongated tubular member can decrease from the proximal end to the distal end. Alternatively, the stiffness of the elongated tubular member can increase from the proximal end to the distal end. In some examples, the stiffness gradients can transition gradually along the length of the elongated tubular member. A transition of stiffness, in certain examples, can prevent localized stiffness and potential kink points.

In addition, the strength, flexibility, and/or stiffness of the elongated tubular member can be varied through the use of the number of wires, different wire materials or wire configurations including, but not limited to braided, coiled, doubled, and split-coil configurations. For example, the wire can reinforce the polymeric matrix and thus the inflation lumen can be supported and protected from kinking. The wire configuration for the inflation lumen can be conducted for single, dual, and triple lumen. The braided wire configuration can be present below the inflation lumen, whereas, the coil configuration can be present above and/or around the inflation lumen. Additionally, the wire configuration can consist of a number of wires and wrapping configuration to meet the needs of flexibility and structural support of the inflation lumen. The wire configuration can be a doubled wire configuration. The wire configuration can include a split wire configuration wherein the wires are braided above and below the inflation lumen. Additionally, the wire configuration can include a dual wire with a diamond design over the length of the elongated tubular member and a dual coil design over the inflation lumen axis. The individual wires themselves made be round, square or rectangular in profile.

The elongated tubular member can include an outer jacket covering at least a portion of the wrapped wires, providing a reduced friction outer surface of the elongated tubular member. When the catheter is navigated through vasculature, the outer jacket can be effective to provide a smooth surface for contacting the interior of blood vessels without harming or abrading the vessels or generating undue friction force that would resist the catheter being delivered to a treatment site.

The elongated tubular member can include a strike layer covering at least a portion of the inflation lumen. The strike layer can be positioned between the inflation lumen and overlapping braid wires to reduce the likelihood of rupture, pin holes, and abrasion due to movement of the wires over the inflation lumen. The strike layer can include a Pebax®, urethane material, PU, and the like. The strike layer can provide a protection layer around the inflation lumen, minimizing the risk of rupture, pin holes, and abrasion.

The inflation lumen and the strike layer can include materials compatible such that if the inflation lumen becomes compromised the strike layer is effective to seal the compromised portion, thereby preventing the inflation lumen from leaking. In some applications a strike layer constructed of Pebax®, urethane material can be effective at sealing compromised portion of an inflation lumen including PTFE (e.g. dipped PTFE).

The polymer strike layer can include materials compatible with materials of the outer jacket. The outer jacket is laminated into place. During manufacturing, the strike layer and the outer jacket can melt into each other during the manufacturing process.

The polymer strike layer can include materials compatible with the inner core. The inner core can be made of PTFE and the strike layer can be made with PU.

The balloon can be located at the distal end of the elongated tubular member. The balloon can enable the securing of the catheter, the arresting of blood flow, and the generating of improved aspiration efficacy when aspirating the main central lumen of the catheter.

The balloon can be connected to the elongated tubular member by a weld joint, the weld joint being in some embodiments made between the balloon and an intermediate material hereinafter referred to as a tie-layer. The balloon can be made from a number of materials and can be coated, non-coated, tacky, or non-tacky. In some known devices, catheter balloons are made from silicone as this material has a very high recoverable elastic strain and can be used to make a very soft and compliant balloon. However, silicone is a very difficult material to join to other materials. It can require an adhesive joint which can add to the stiffness and profile of the distal end of the catheter. Recent developments in polymer formulations have resulted in new polymeric elastomeric alloys which have similar material properties to silicone, but can be melted, extruded and welded to other materials. The catheter of this invention preferably includes a balloon made from a blend of ChronoPrene® and urethane materials (such as Polyblend 1100 from AdvanSource Biomaterials), which can be welded to other similar materials, enabling a much more flexible and low-profile construction. The successful creation of such a weld can be further assisted by providing another material (a tie-layer) made from a blend of the balloon material and either a urethane or a Pebax® material. This tie-layer is thus configured to be compatible with both the balloon material and the material used in the construction of the outer layer of the elongate tubular member (the jacket material), allowing much better reflow behavior and much better welds than could be attained by welding the balloon directly to the jacket material.

The balloon can be designed as a seamless balloon. The seamless balloon can be designed such that the balloon can reach or extend beyond the distal end of the elongated tubular member and minimize any dead space at the distal end of the catheter.

The seamless balloon's profile and/or shape can be constrained in any number of ways, including, but not limited to on one side of the elongated tubular member by one or more bonds. The bond or bonds can be in any number of shapes and or patterns. The bond can ensure that when the seamless balloon is inflated it does not inflate circumferentially. The bond could ensure that when inflated the seamless balloon has more than one section.

The bonded seamless balloon can facilitate the retrieval of medical devices through the inner hollow lumen maximizing clot capture while minimizing the catching of soft clots. In known balloon guide catheters, soft clots can shear off the distal end of the catheter due to "dead space" between the catheter and blood vessel wall, distal the balloon. On deflation of the balloon of a known balloon guide catheter, in some instances, these soft clots can travel distally and result in embolization of distal vessels potentially resulting in additional procedural time or impact to patient health. The bonded seamless balloon can be shaped to have minimal or to no "dead space" thereby reducing the likelihood of aforementioned complications.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 16A is a cross section illustration of an elongated tubular member of the present invention having dual inflation lumens and reinforcing wires.

FIG. 16B is a cross section illustration of an elongated tubular member of the present invention having dual inflation lumens and reinforcing wires.

FIG. 16C is a cross section illustration of an elongated tubular member of the present invention having three inflation lumens.

FIG. 16D is a cross section illustration of an elongated tubular member of the present invention having dual inflation lumens positioned on opposite sides of the circumference of the elongated tubular member.

DETAILED DESCRIPTION

Figure 1:
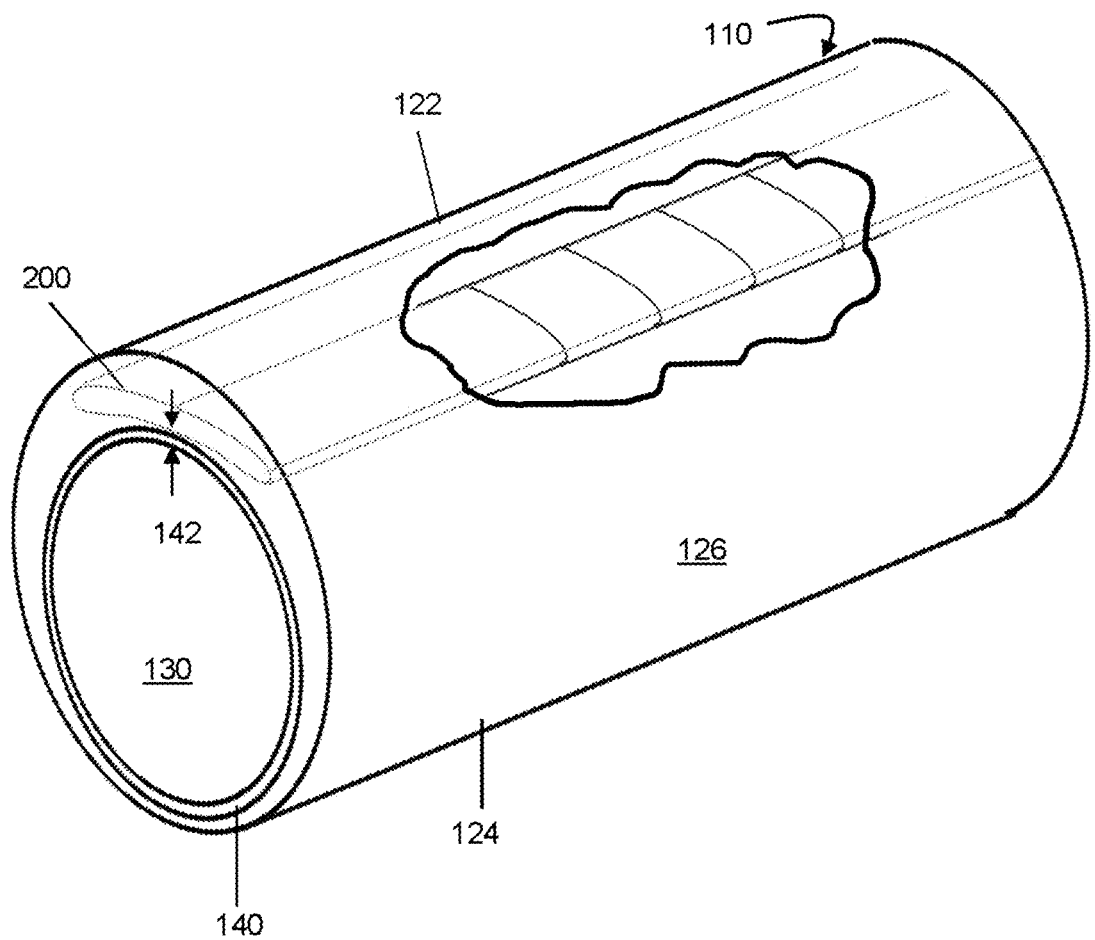
FIG. 1 is a top-front perspective illustration of a portion of the elongated tubular member of the present invention.

FIG. 1 illustrates the catheter 100. As illustrated, the catheter 100 can have an elongate tubular member 110. The elongated tubular member 110 can have a proximal end 112, a distal end 114, a top 122, a bottom 124, and an outer surface 126, two inner surfaces of an inner hollow lumen 130, an inflation lumen 200, and an inner core 140. The inner hollow lumen 130 can extend from the proximal end 112 of the elongated tubular member 110 to the distal end 114 of the elongated tubular member 110. The inflation lumen 200 can extend between the proximal end 112 of the elongated tubular member 110 to the distal end 114 of the elongated tubular member 110. The inflation lumen 200 can be smaller than the inner hollow lumen 130. The inflation lumen 200 can be located approximately at the top 122 of the elongated tubular member 110 or the bottom 124 of the elongated tubular member and outside the inner hollow lumen 130.

Figure 2A:
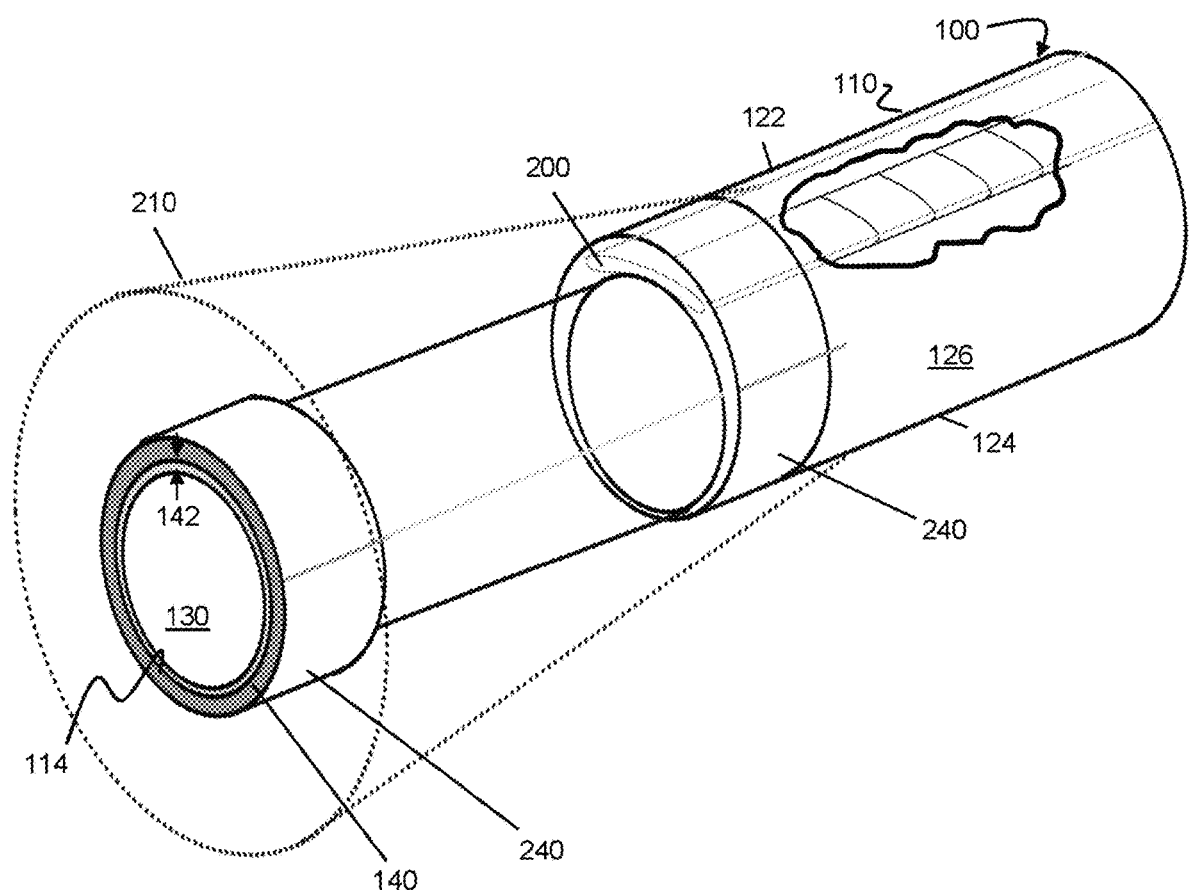
FIG. 2A is a top-front perspective illustration of the inflated seamless balloon of the present invention.

FIG. 2A illustrates an inflated, seamless balloon 210 profile of the catheter 100. The seamless balloon 210 can be secured to the elongated tubular member 110 by a tie-layer 240. The seamless balloon 210 can extend beyond the distal end 114 of the elongated tubular member 110. The seamless balloon 210 can be inflated as illustrated.

The tie-layer 240 can include a material to which both the balloon and the shaft jacket material can be welded. The jacket can include a polyurethane material at least over a few centimeters of a distal portion of the catheter 100. The tie-layer 240 can include a 50/50 blend of the balloon material and the polyurethane jacket material. The balloon 210 can be welded onto the jacket.

Figure 2B:
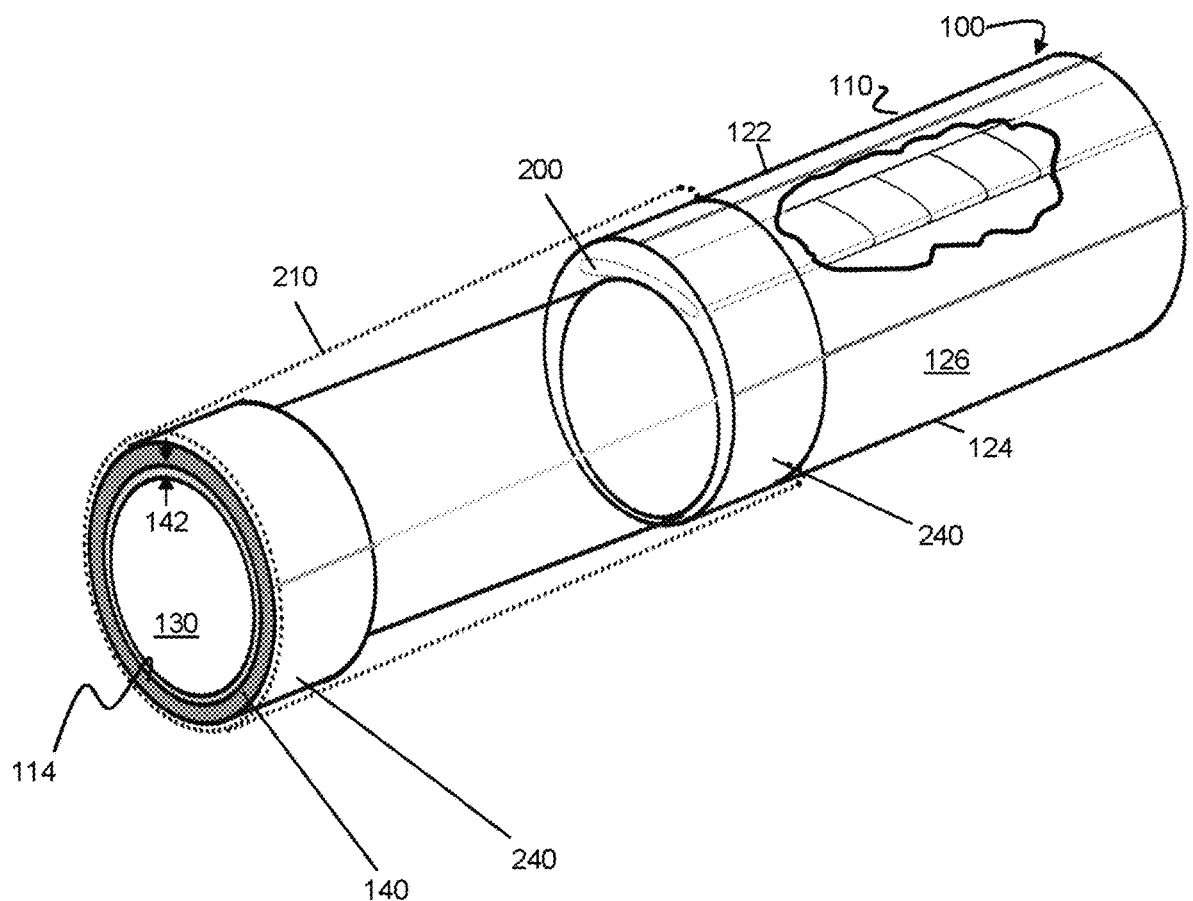
FIG. 2B is a top-front perspective illustration of the deflated seamless balloon of the present invention.

FIG. 2B illustrates a deflated, seamless balloon 210 profile of the catheter 100. The seamless balloon 210 can be secured to the elongated tubular member 110 by a tie-layer 240. The seamless balloon 210 can extend beyond the distal end 114 of the elongated tubular member 110. The seamless balloon 210 can be deflated as illustrated.

Figure 3:
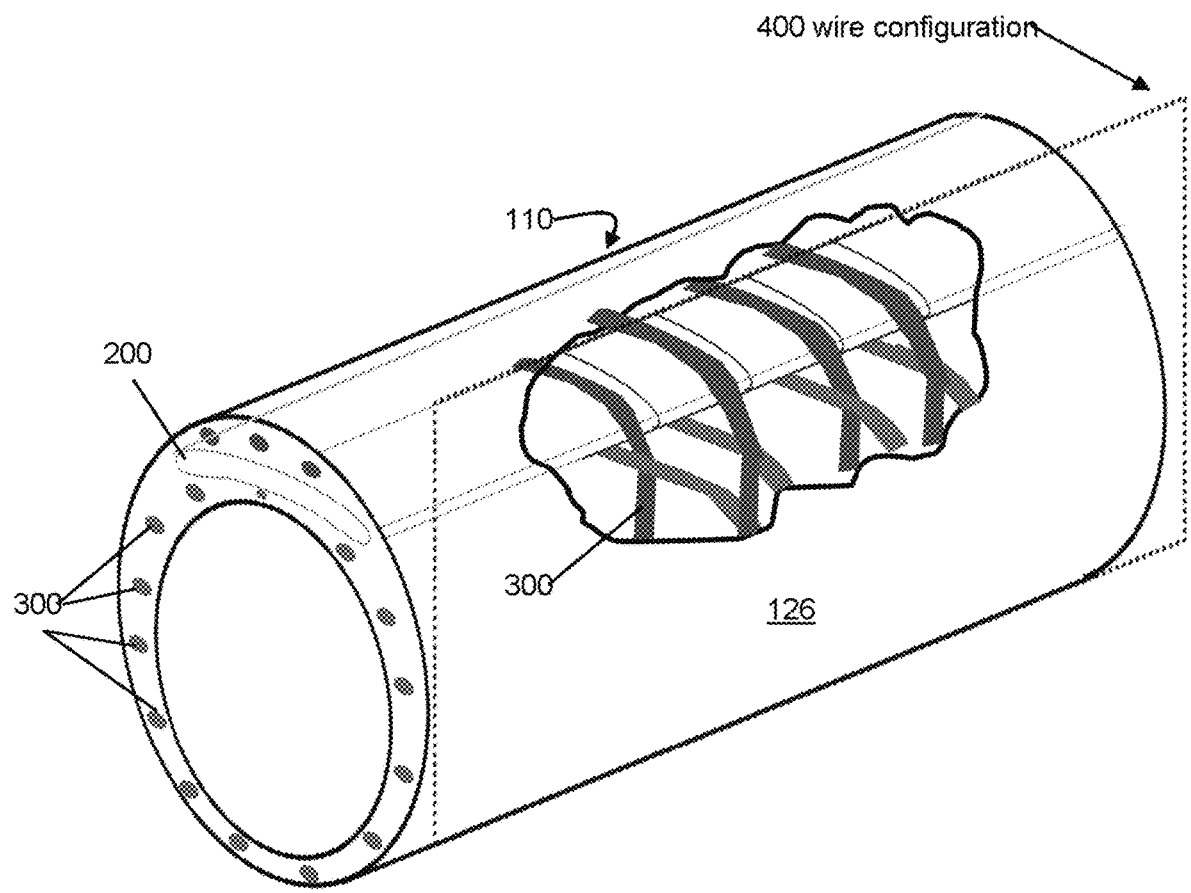
FIG. 3 is a top-front perspective illustration of the inflation lumen kink protection wire configuration cut-out of the present invention.

FIG. 3 illustrates a wire configuration 400 of wire 300 of the inflation lumen kink protection of the catheter 100 including a cross-section of the elongated tubular member 110. The wire configuration 400 can have the wire 300, which can be located within the elongated tubular member 110, go above and below the inflation lumen 200. The wire configuration 400 allows for a more flexible catheter 100 and transfer of torque from the proximal end 112 to the distal end 114 of the catheter 100. This permits the user to apply torque to the proximal end 112 to more easily orientate the distal end 114 in the needed direction to advance the catheter through the vasculature while still maintaining the integrity of the inflation lumen 200. Note that certain catheters 100 can be advanced from a patient's inner thigh, over the cardiac arch, and up into the neurovascular inside the patient's skull and thus the distance and tortuosity can be significant.

The wiring 400 is acting similarly to rebar in concrete reinforcement of an air plane hangar or ground bunker, supporting an arched structure. Reinforcing the wire network 400 with the polymer matrix of the elongated tubular member 110 above and below the inflation lumen 200 helps reduce or prevent kinking.

During manufacture, the braid wires 300, when encountering the inflation lumen 200 on the braiding machine, separate out to go over and below the inflation lumen 200. The wire reinforces the polymeric matrix of the catheter 100 and thus a thin PTFE sleeve or lumen with standard sleeve such as PE or PET or FEP or no sleeve (i.e. a "raw extrusion lumen") is supported and protected from kinking. In some examples, the braid 200 essentially occurs along the majority of the elongated tubular member 110 to enhancing torque ability and push ability of the shaft. Other examples can change the coil geometry to lower the flexural stiffness of the catheter 100 as compared to the braid. The PTFE lumen adds to the flexural stiffness and the coils help to lower this stiffness. The stiffness can deliver a preference for the device to orientate during insertion of the device and the addition of the coils instead of the braid lessens this "whip" orientation around a bend in the vascular.

The example wire protection for the inflation lumen 200 can be conducted for dual and triple lumens within the catheter (not illustrated). In other examples, the wire configuration 400 is ideally suited to a single lumen of particular arc radius dimensions.

The cross-section of the elongated tubular member 110 illustrates the positioning (i.e. wire configuration 400) of the wires 300 above and below the inflation lumen 200. The wire configuration 400 contributes to the strength and reduces the stiffness of the catheter 100. Additionally, the wire configuration 400 helps lower the flexural stiffness of the catheter compared to the wires 300. The inflation lumen 200 can increase the stiffness of the catheter 100 and the wire configuration can lower the stiffness and/or increase the flexibility. The stiffness and/or flexibility can deliver a preference for the device to orientate during insertion of the devices and the wire configuration 400 lessens the challenges seen with prior art devices.

The stiffness and flexibility can be also be altered by using different materials for each portion of the shaft, each portion being of a different stiffness or durometer, in addition to using various numbers of wires 300, different wire 300 materials or wire configurations 400 including, but not limited to braided, coil, doubled 500, and split-coil 510 configurations. The braided wire configuration 400 can be present below the inflation lumen 200, whereas, the coil configuration can be present above and/or around the inflation lumen 200. Additionally, the wire configuration 400 can consist of any number of wires 300 including the doubled wire configuration 500. The wire configuration 400 can include a split wire configuration 510 wherein the wires 300 are braided above and below the inflation lumen 200. Alternately, the elongated tubular member 110 can be made of the same material and additional layers or additives can be provided to control the individual stiffness. These examples can be combined to provide the needed flexibility and/or stiffness. Note that the elongated tubular member can have a uniform stiffness across its length, or it can vary. As an example, the stiffness of the elongated tubular member 110 can decrease from the proximal end 112 to the distal end 114. As another example, the stiffness of the elongated tubular member 110 can increase from the proximal end 112 to the distal end 114. Any transition of stiffness, in certain examples, can prevent localized stiffness.

Figure 4A:
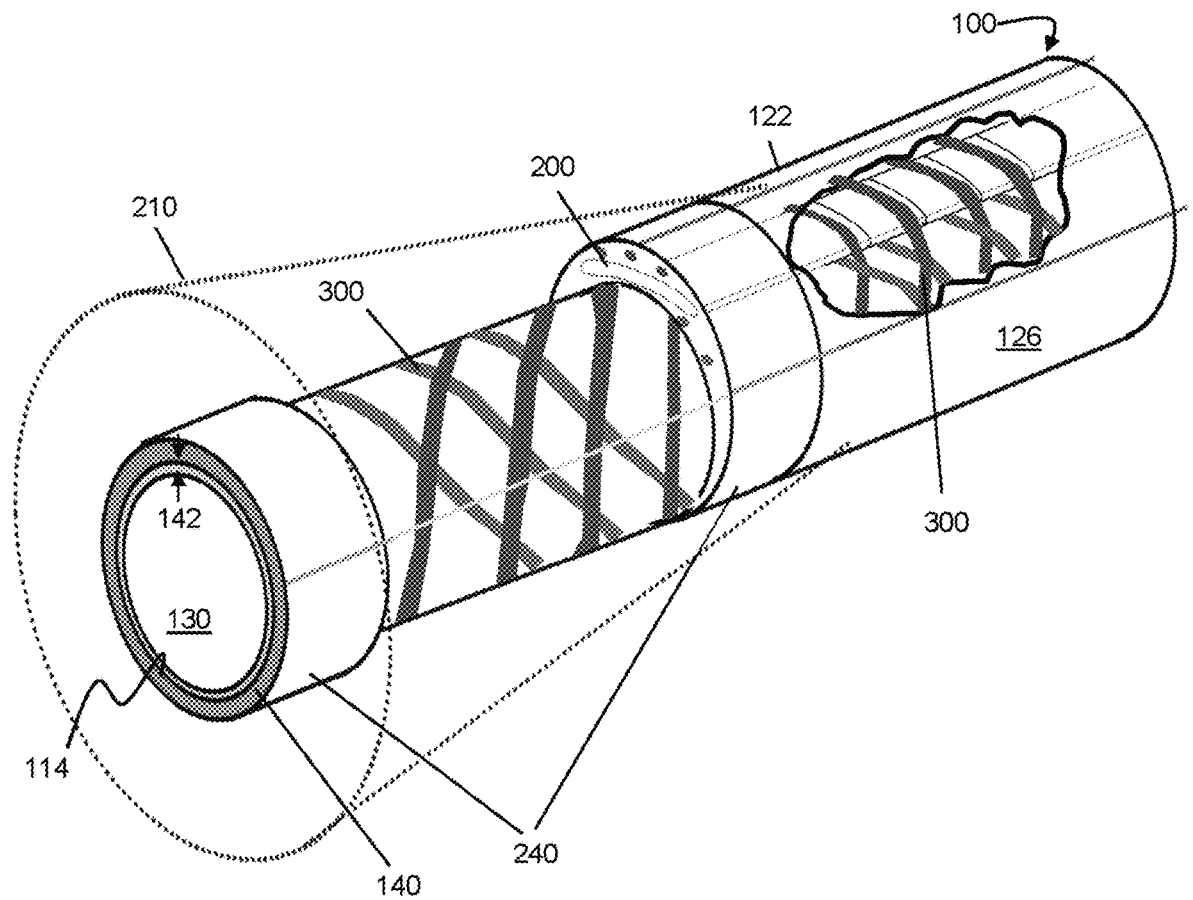
FIG. 4A is a top-front perspective illustration of the inflation lumen kink protection wire configuration and inflated seamless balloon of the present invention.

FIG. 4A illustrates an inflated, seamless balloon 210 profile and wire 300 wire configuration 400 of the catheter 100. The seamless balloon 210 can be secured to the elongated tubular member 110 by a tie-layer 240. The seamless balloon 210 can extend beyond the distal end 114 of the elongated tubular member 110. The seamless balloon 210 can be inflated as illustrated. The reinforcement of the wire configuration 400 by the wire 300 does not impede the inflation of the seamless balloon 210. In this example, the seamless balloon 210 can inflate concentric to inner hollow lumen 130, or where the outer edge of the inflated balloon is approximately equidistant from a center of the inner hollow lumen 130. There can be some eccentricity based on the location of the inflation lumen 200.

Figure 4B:
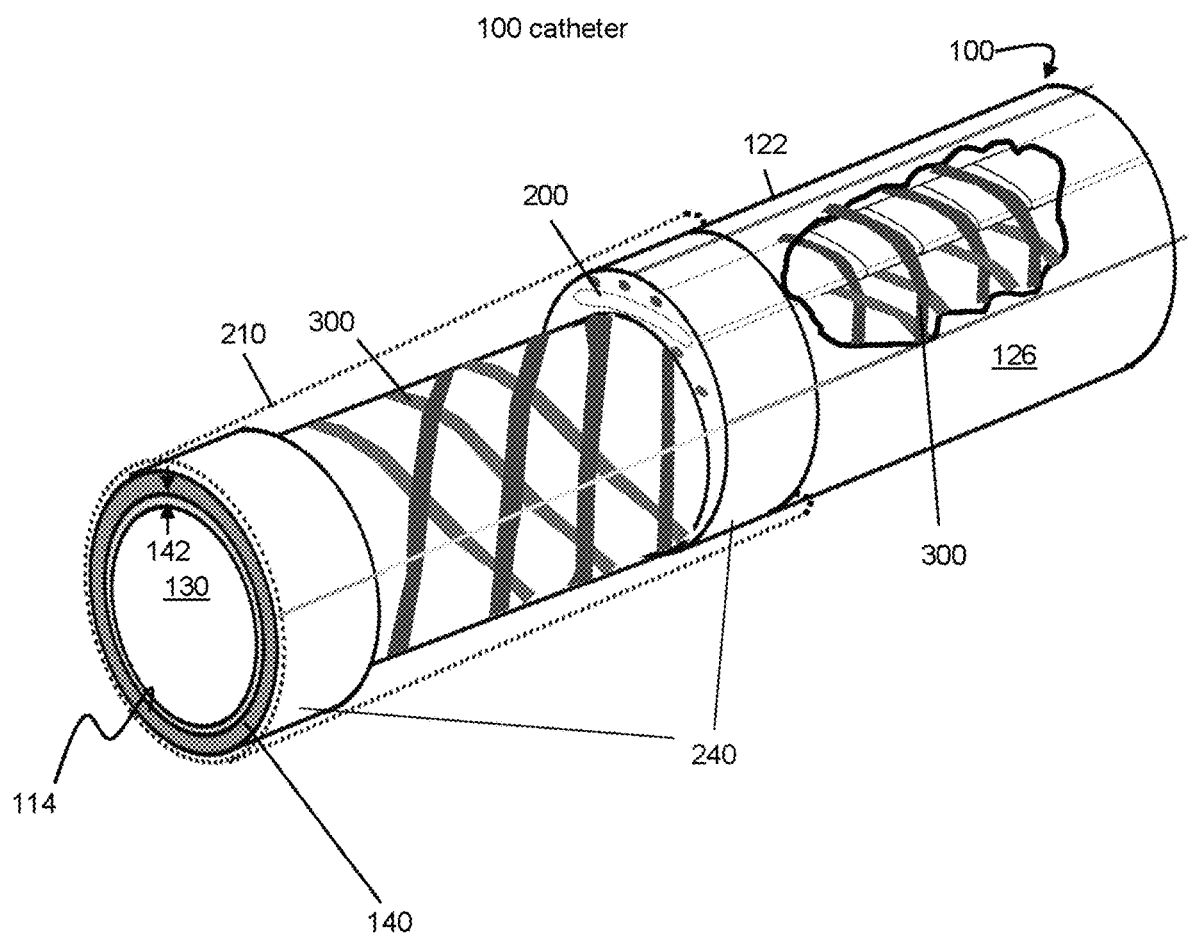
FIG. 4B is a top-front perspective illustration of the inflation lumen kink protection wire configuration and deflated seamless balloon of the present invention.

FIG. 4B illustrates a deflated, seamless balloon 210 profile and wire 300 wire configuration 400 of the catheter 100. The seamless balloon 210 can be secured to the elongated tubular member 110 by a tie-layer 240. The seamless balloon 210 can extend beyond the distal end 114 of the elongated tubular member 110. The seamless balloon 210 can be deflated as illustrated. The reinforcement of the wire configuration 400 by the wire 300 does not impede the deflation of the seamless balloon 210. In some examples, when deflated, the seamless balloon 210 can have the same outer profile as the elongated tubular member 110, giving the catheter 100 a uniform diameter/profile for insertion and removal.

Figure 5:
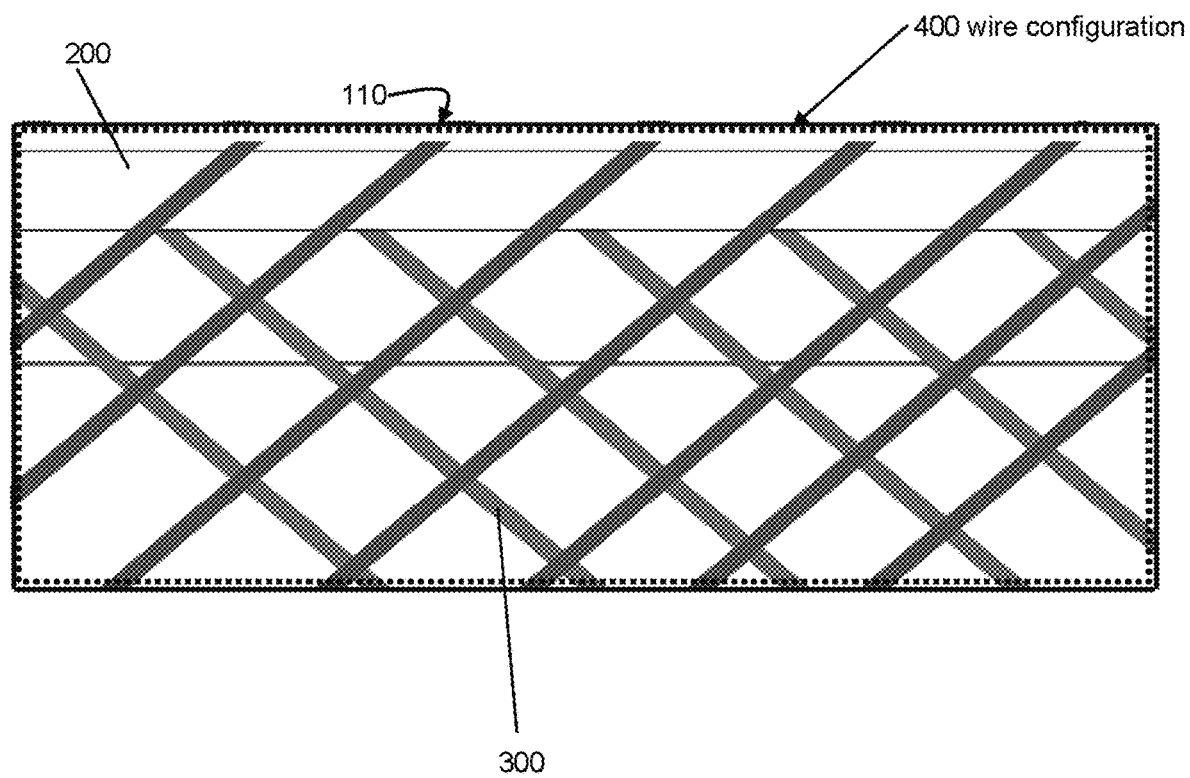
FIG. 5 is a side view illustration of the inflation lumen kink protection wire configuration of the present invention.

FIG. 5 illustrates a sideview of a braided and coil wire configuration 400 of the catheter 100. The wire 300 can go above and below the inflation lumen 200. The braided wire configuration 400 allows for a stiffer catheter 100 while minimizing cost and weight among many other factors. The braided design facilitates the transfer of torque from the proximal end 112 to the distal end 114 of the catheter 100. This permits the user to apply torque to the proximal end 112 to more easily orientate the distal end 114 in the needed direction to advance the catheter through the vasculature while still maintaining the integrity of the inflation lumen 200.

Figure 6A:
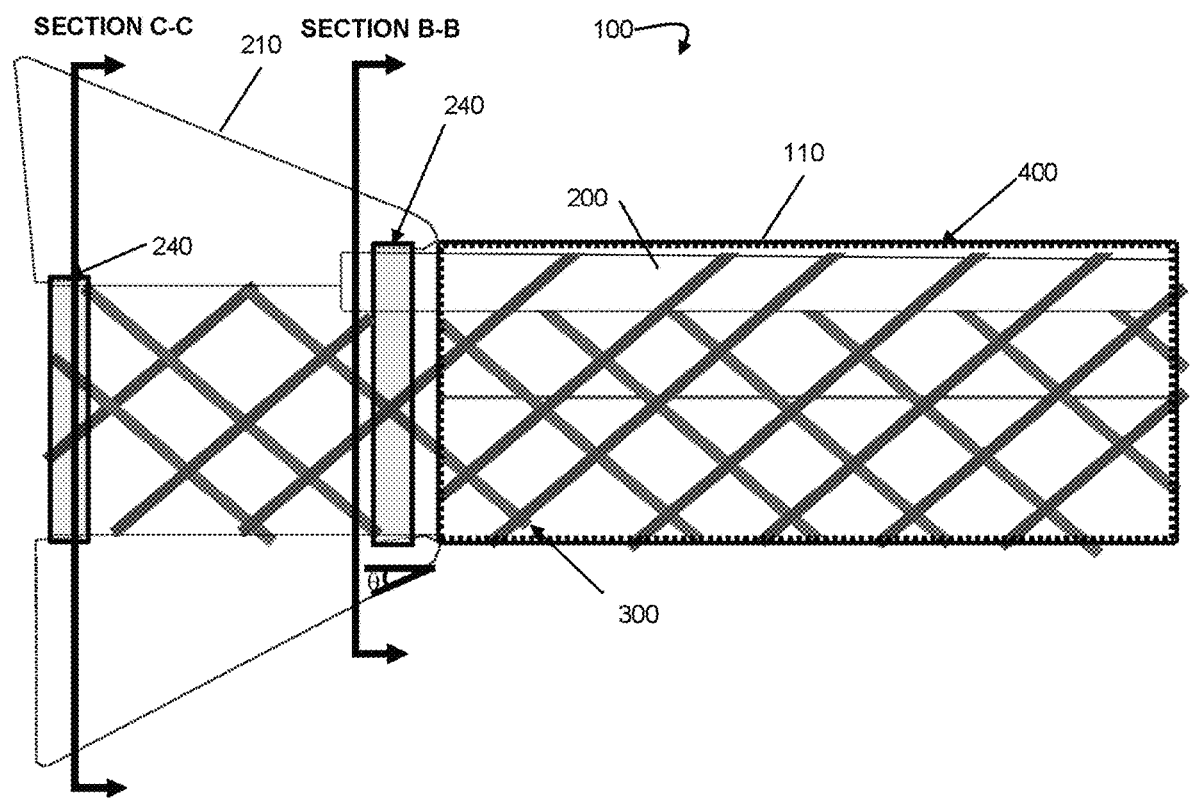
FIG. 6A is a side view illustration of the inflation lumen kink protection wire configuration and inflated seamless balloon of the present invention.

FIG. 6A illustrates an inflated, seamless balloon 210 profile and braided and coil wire configuration 400 of the catheter 100. The seamless balloon 210 can be secured to the elongated tubular member 110 by a tie-layer 240. The seamless balloon 210 can extend beyond the distal end 114 of the elongated tubular member 110. The seamless balloon 210 can be inflated as illustrated. The reinforcement of the braided, wire configuration 400 by the wire 300 does not impede the inflation of the seamless balloon 210.

Figure 6B:
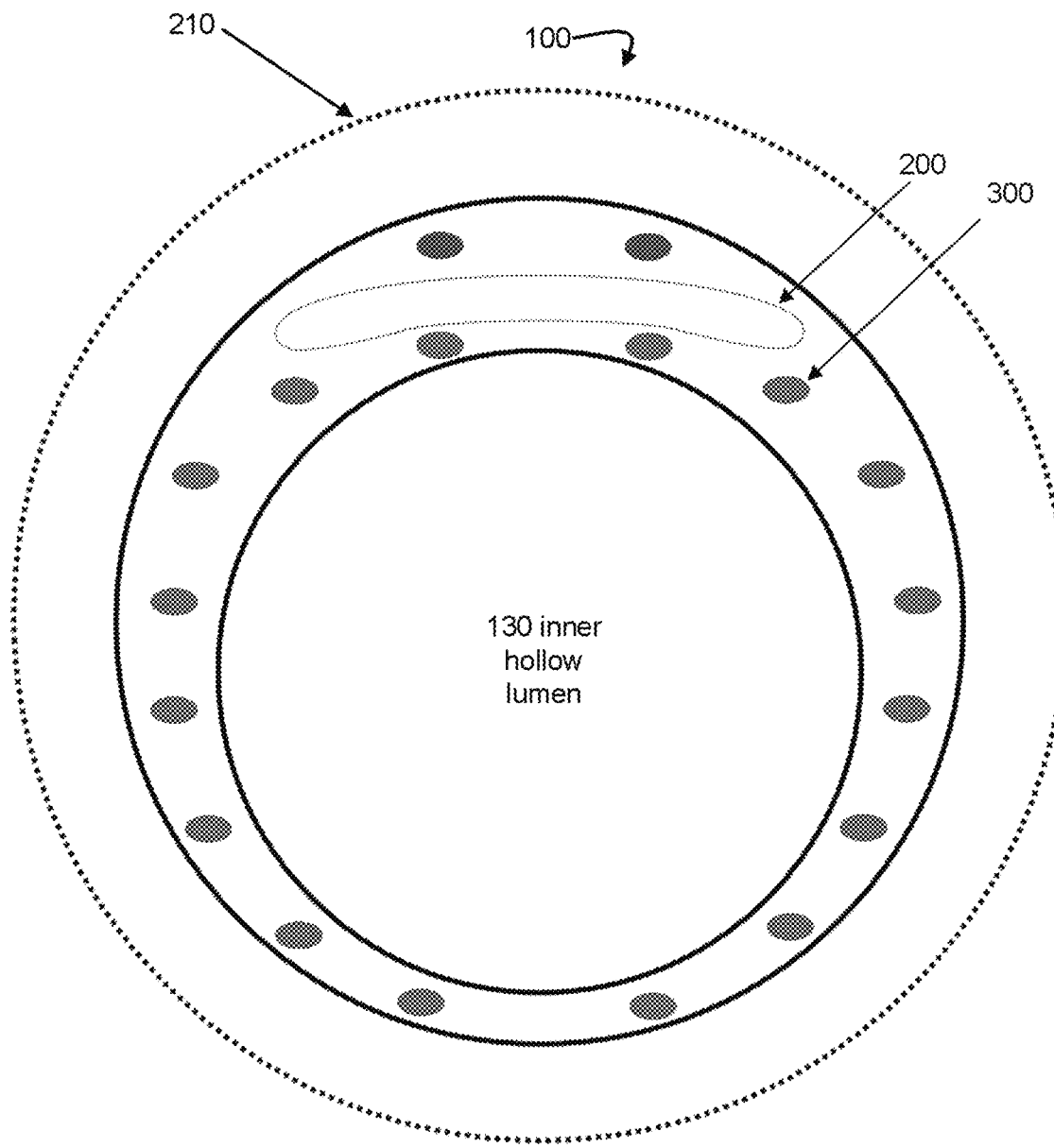
FIG. 6B is a cross-sectional view illustration of the balloon guiding catheter, inflated seamless balloon, and inflation lumen kink protection wire configuration of the present invention.

FIG. 6B illustrates the cross-section of FIG. 6A across Section B-B depicting an inflated, seamless balloon 210 profile and wire configuration 400 of the catheter 100. The cross-section depicts the location of the wires 300 above and below the inflation lumen 200 within the elongated tubular member 110. The cross-section also illustrates the relative positions of the seamless balloon 210, inflation lumen 200, and wire 300 and how the wire configuration 400 does not impede the inflation of the seamless balloon 210.

Figure 6C:
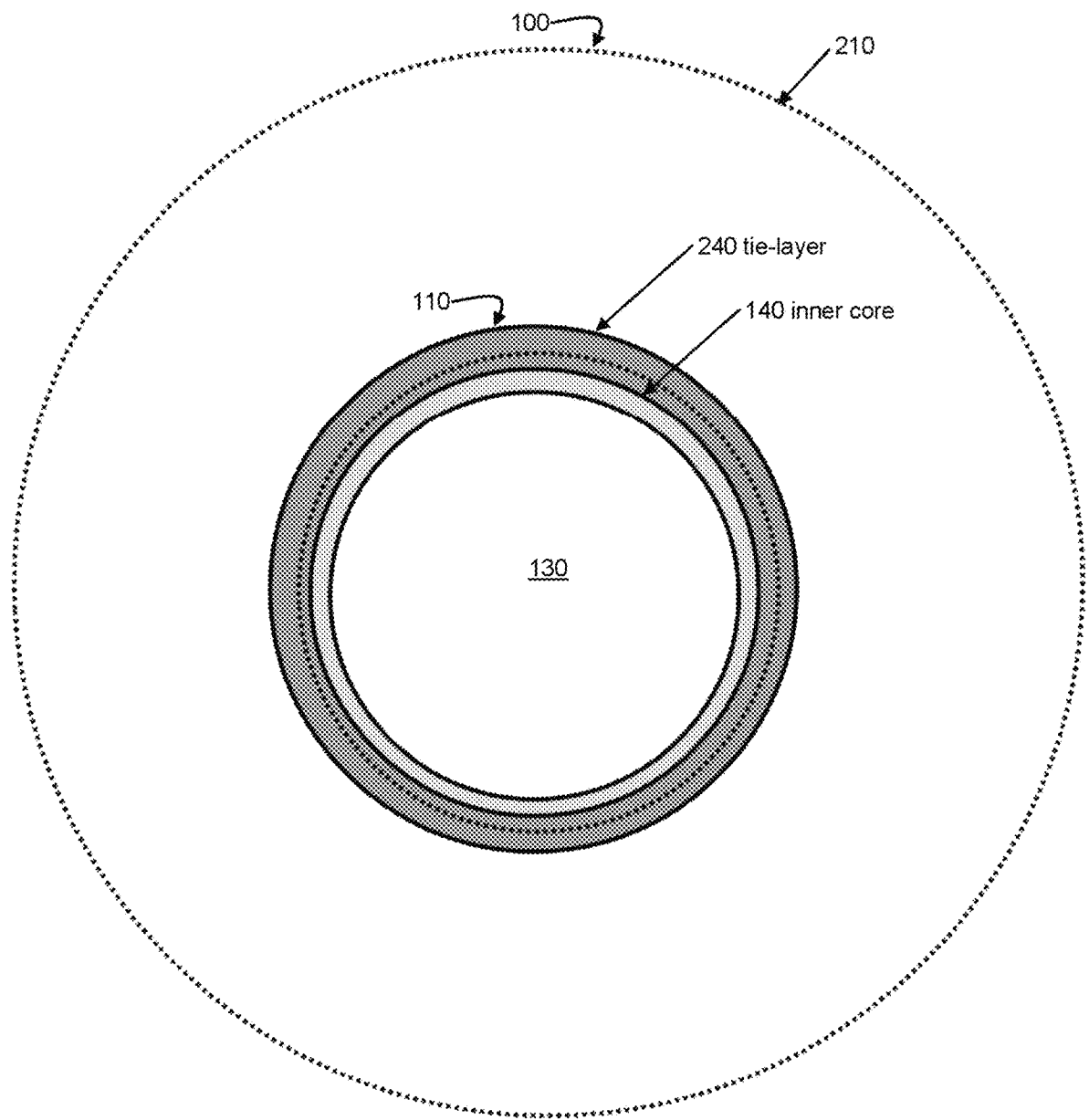
FIG. 6C is a cross-sectional view illustration of the balloon guiding catheter and inflated seamless balloon of the present invention.

FIG. 6C illustrates the cross-section of FIG. 6A across Section C-C depicting an inflated, seamless balloon 210 profile and wire configuration 400 of the catheter 100. The cross-section illustrates the relative positions of the seamless balloon 210, tie-layer 240, inner core 140, and inner hollow lumen 130 and how tie-layer 240 does not impede the inflation of the seamless balloon 210.

The balloon 210 when inflated can have an aspect ratio and height that effectively blocks the blood vessel while minimizing fluid shear. The balloon can have a height of about 0.004" to about 0.008". In some applications, the balloon can have a height of about 0.0055" to about 0.0065". The balloon 210 when inflated can have a substantially trapezoidal profile when viewed from the side as illustrated in FIG. 6A, tapering to a smaller width on the proximal end of the balloon 210 and expanding to a larger width when on the distal end of the balloon. The tapering can define an angle $\theta$ that is the angle between an angled surface of the balloon and a line parallel to the tubular elongated member 110. The balloon 210 when inflated can define an angle $\theta$ less than 70° when used on a tubular elongated member 110 having inner lumen 130 of about 0.088" in diameter. The balloon 210 when inflated can define an angle $\theta$ of about 60° to about 65° when used on a tubular elongated member 110 having inner lumen 130 of about 0.088" in diameter.

Figure 7A:
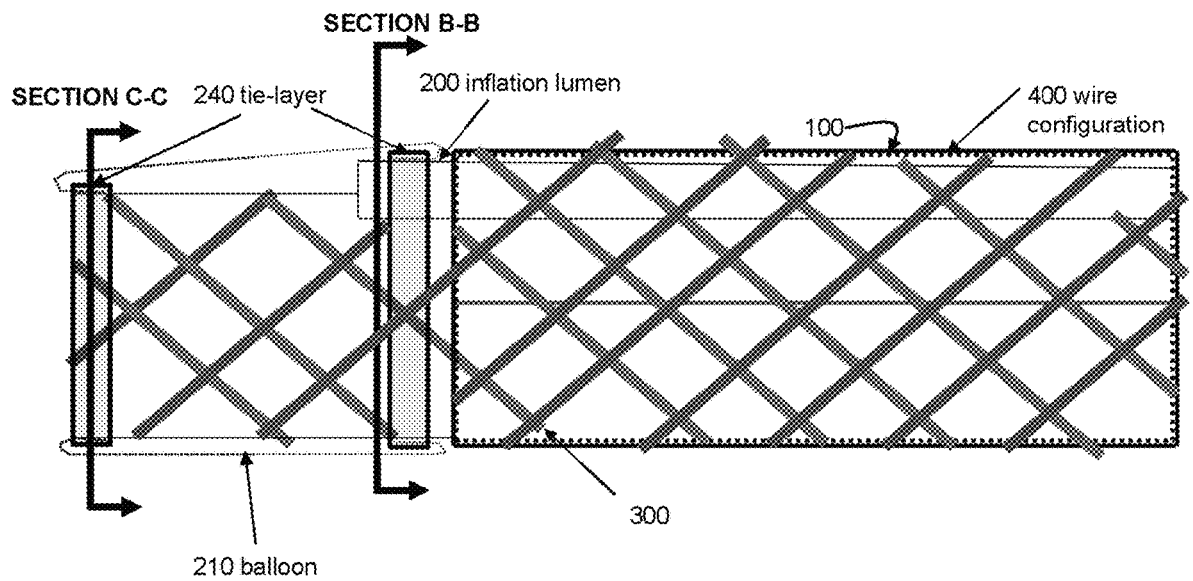
FIG. 7A is a side view illustration of the inflation lumen kink protection wire configuration and deflated seamless balloon of the present invention.

FIG. 7A illustrates a deflated, seamless balloon 210 profile and braided and coil wire configuration 400 of the catheter 100. The seamless balloon 210 can be secured to the elongated tubular member 110 by a tie-layer 240. The seamless balloon 210 can extend beyond the distal end 114 of the elongated tubular member 110. The seamless balloon 210 can be deflated as illustrated. The reinforcement of the braided and coil wire configuration 400 by the wire 300 does not impede the deflation of the seamless balloon 210.

Figure 7B:
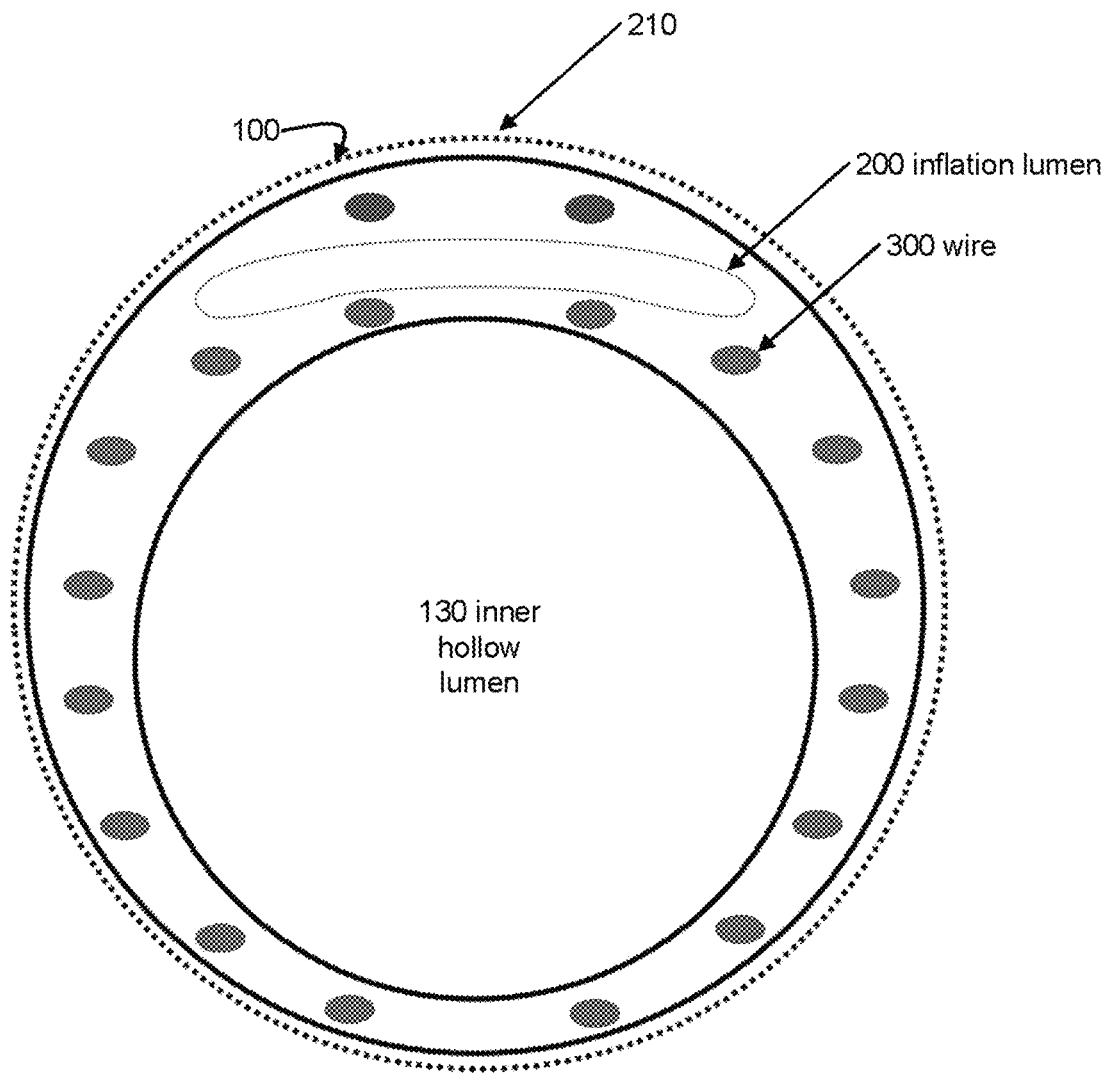
FIG. 7B is a cross-sectional view illustration of the balloon guiding catheter, deflated seamless balloon, and inflation lumen kink protection wire configuration of the present invention.

FIG. 7B illustrates the cross-section of FIG. 7A across Section B-B depicting a deflated, seamless balloon 210 profile and wire configuration 400 of the catheter 100. The cross-section depicts the location of the wires 300 above and below the inflation lumen 200 within the elongated tubular member 110. The cross-section also illustrates the relative positions of the seamless balloon 210, inflation lumen 200, and wire 300 and how the wire configuration 400 does not impede the deflation of the seamless balloon 210.

Figure 7C:
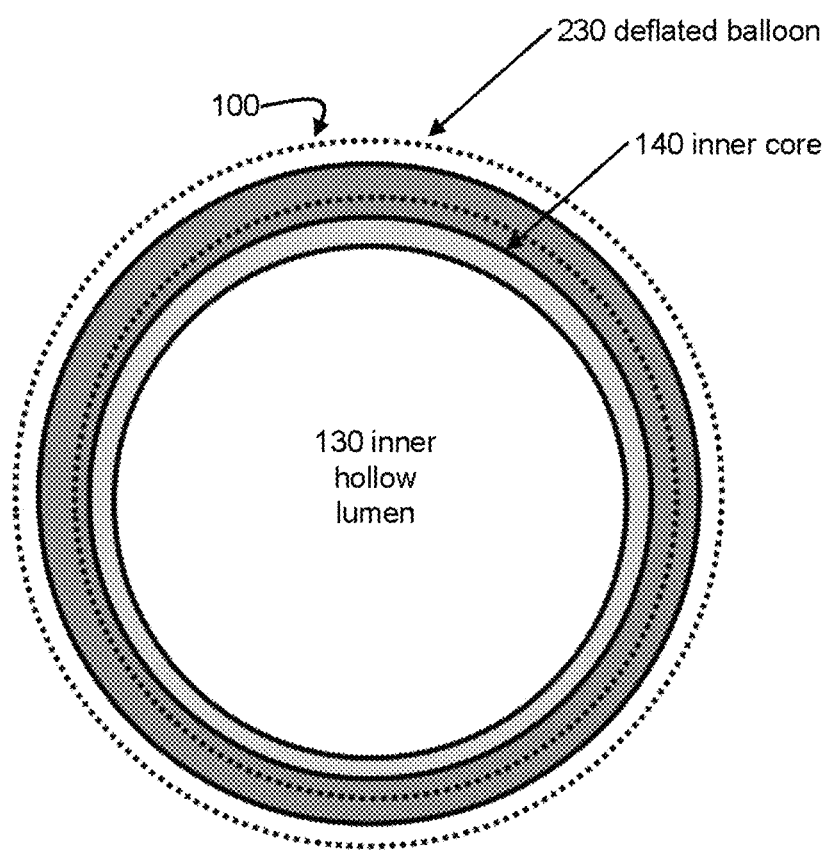
FIG. 7C is a cross-sectional view illustration of the balloon guiding catheter and deflated seamless balloon of the present invention.

FIG. 7C illustrates the cross-section of FIG. 7A across Section C-C depicting a deflated, seamless balloon 210 profile and wire configuration 400 of the catheter 100. The cross-section illustrates the relative positions of the seamless balloon 210, tie-layer 240, inner core 140, and inner hollow lumen 130 and how tie-layer 240 does not impede the deflation of the seamless balloon 210.

Figure 8:
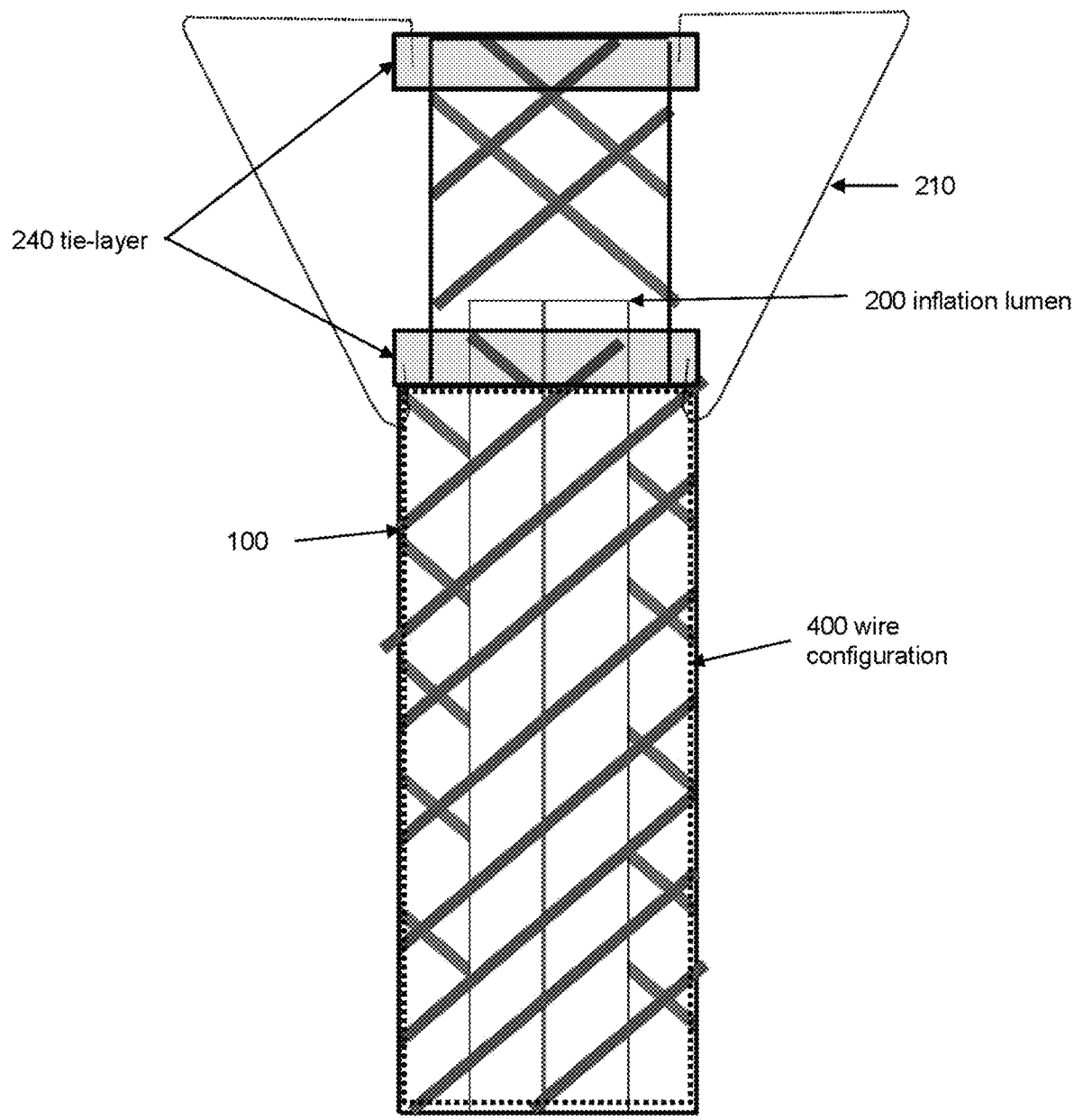
FIG. 8 is a top view illustration of the balloon guiding catheter, inflated seamless balloon, and inflation lumen kink protection wire configuration of the present invention.

FIG. 8 illustrates a top view depicting an inflated seamless balloon 210 profile and wire configuration 400 of the catheter. The view illustrates the relative positions of the seamless balloon 210, inflation lumen 200, and wire 300 and how the wire configuration 400 does not impede the inflation of the seamless balloon 210. The view also illustrates the coil configuration above the inflation lumen 200.

Figure 9:
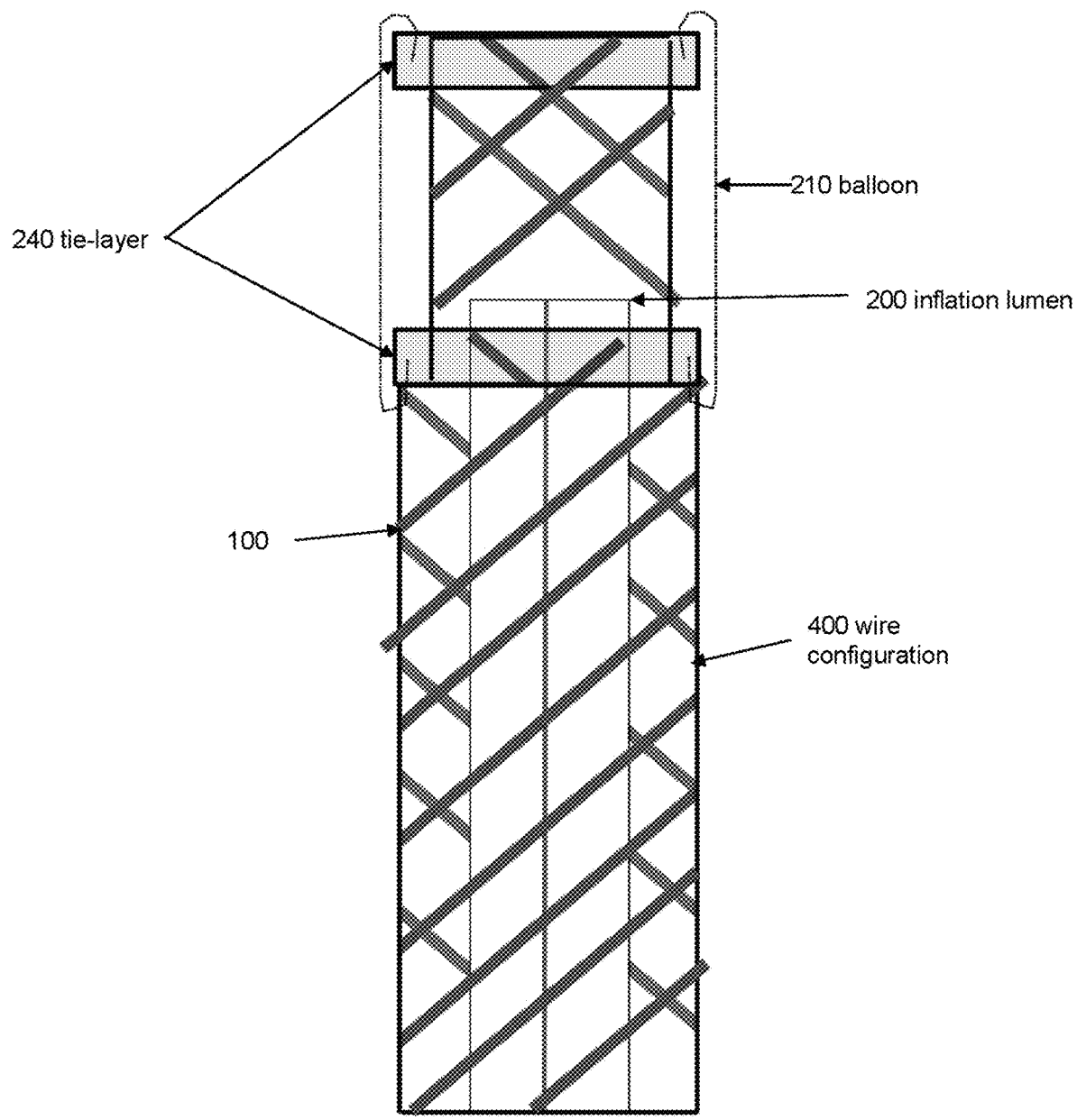
FIG. 9 is a top view illustration of the balloon guiding catheter, deflated seamless balloon, and inflation lumen kink protection wire configuration of the present invention.

FIG. 9 illustrates a top view depicting a deflated seamless balloon 210 profile and wire configuration 400 of the catheter. The view illustrates the relative positions of the seamless balloon 210, inflation lumen 200, and wire 300 and how the wire configuration 400 does not impede the deflation of the seamless balloon 210. The view also illustrates the coil configuration above the inflation lumen 200.

Figure 10:
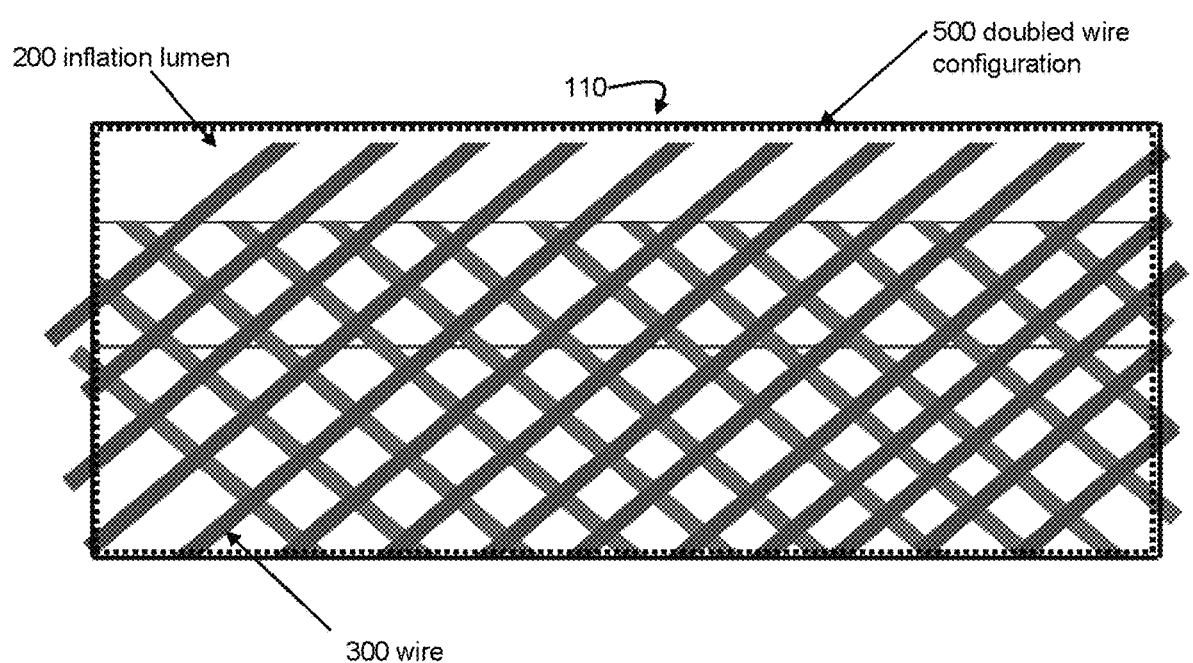
FIG. 10 is a side view illustration of the inflation lumen kink protection additional wire configuration of the present invention.
Figure 11:
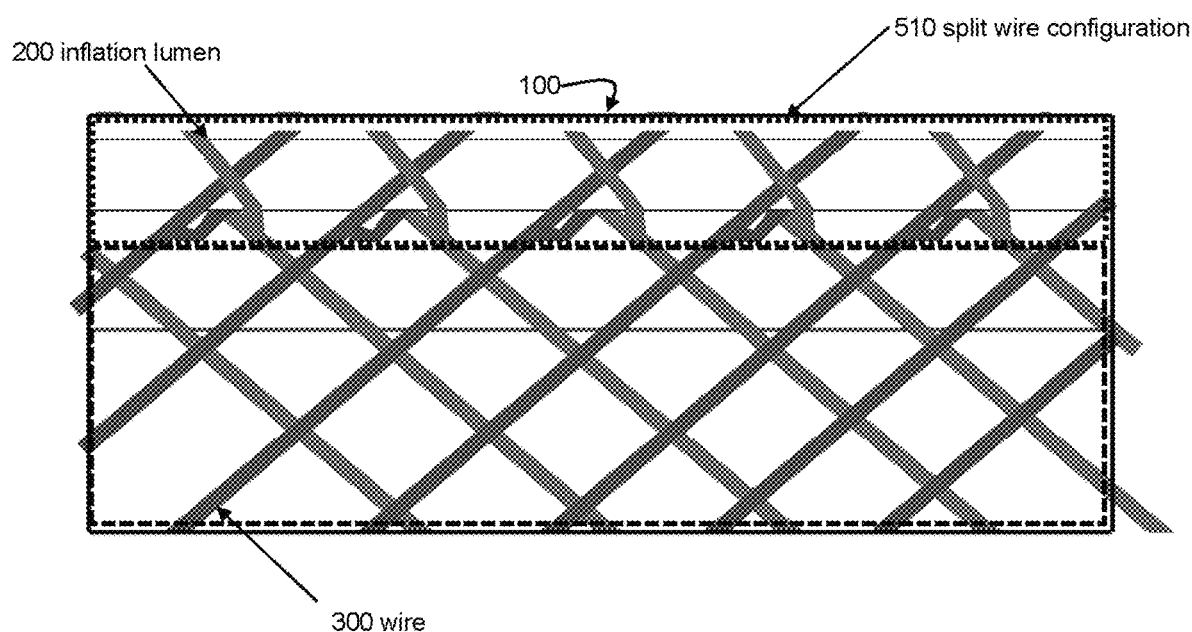
FIG. 11 is a side view illustration of the inflation lumen kink protection split-coil wire configuration of the present invention.

FIGS. 10 and 11 illustrates side views of possible wire configurations 400. Specifically, FIG. 10 illustrates the doubled wire configuration 500 and FIG. 11 illustrates the split wire configuration 510.

Figure 12:
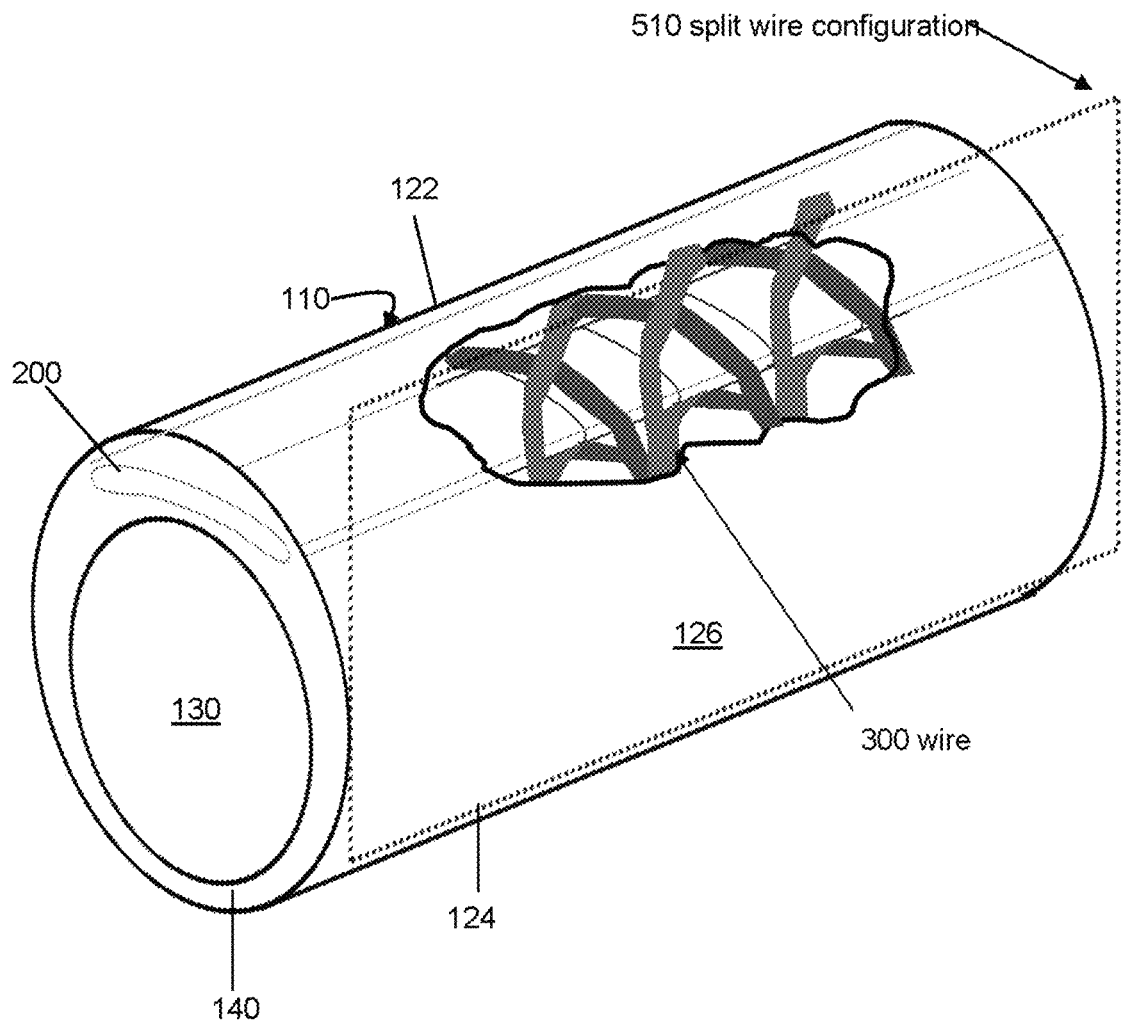
FIG. 12 is a top-front perspective illustration of the inflation lumen kink protection split-coil wire configuration cut-out of the present invention.

FIG. 12 illustrates a split wire configuration 510 of wire 300 of the inflation lumen kink protection of the catheter 100 including a cross-section of the elongated tubular member 110. The wire configuration 400 can have the wire 300, which can be located within the elongated tubular member 110, braided above and below the inflation lumen 200. The split wire configuration 510 allows for a more flexible catheter 100 and transfer of torque from the proximal end 112 to the distal end 114 of the catheter 100. This permits the user to apply torque to the proximal end 112 to more easily orientate the distal end 114 in the needed direction to advance the catheter through the vasculature while still maintaining the integrity of the inflation lumen 200. Note that certain catheters 100 can be advanced from a patient's inner thigh, over the cardiac arch, and up into the neurovascular inside the patient's skull and thus the distance and tortuosity can be significant.

Figure 13A:
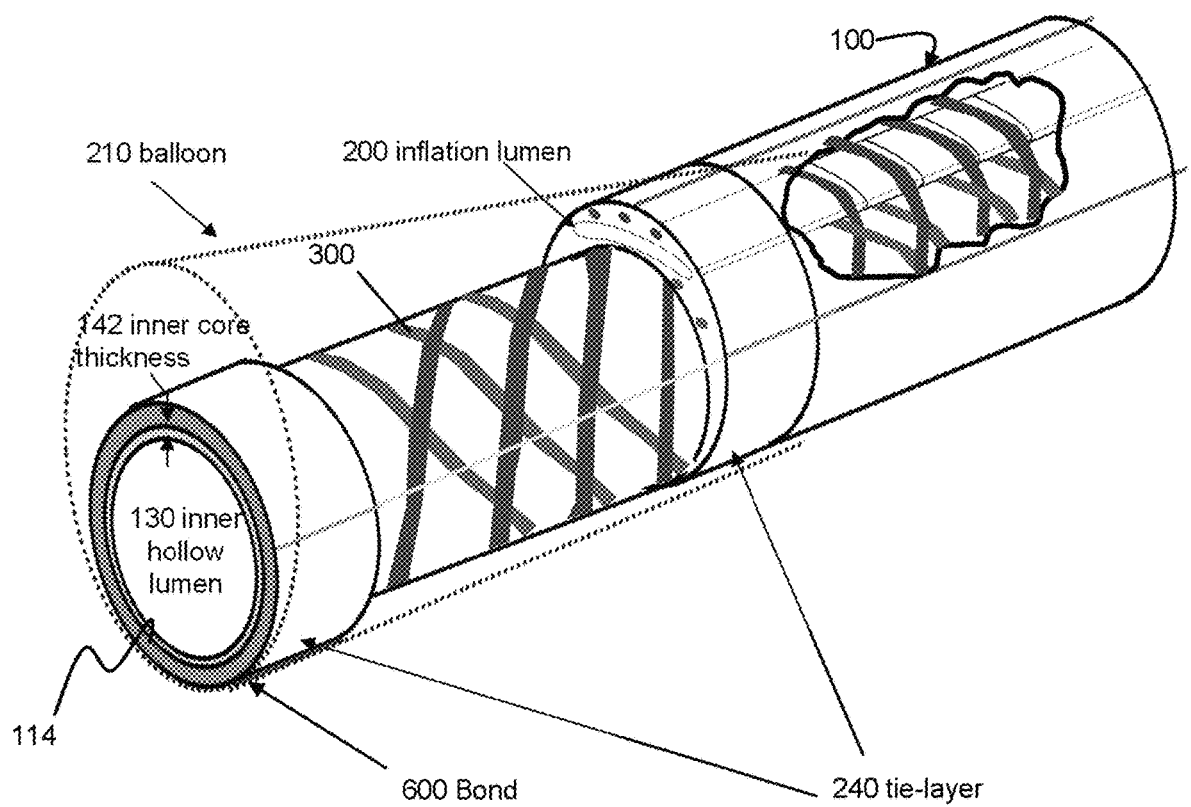
FIG. 13A is a top-front perspective illustration of the bonded, inflated seamless balloon of the present invention.

FIG. 13A illustrates an inflated, bonded 600 seamless balloon 210 profile and wire 300 wire configuration 400 of the catheter 100. The seamless balloon 210 can be secured to the elongated tubular member 110 by a tie-layer 240 and/or bond 600, so that when inflated it does not inflate circumferentially. The seamless balloon 210 can extend beyond the distal end 114 of the elongated tubular member 110. The seamless balloon 210 can be inflated as illustrated. The reinforcement of the wire configuration 400 by the wire 300 does not impede the inflation of the seamless balloon 210.

In one example, the seamless balloon 210 can be constrained on one side of the elongated tubular member 110 by a bond 600. The bond 600 can be in any number of shapes and or patterns. The bond 600 connecting the seamless balloon 210 to the elongated tubular member 110 ensures that the when inflated the seamless balloon 210 does not inflate circumferentially. The bonded 600 seamless balloon 210 facilitates the retrieval of medical devices through the inner hollow lumen 130 maximize clot capture while minimizing the catching of soft clots. Soft clots can shear off the catheter 100 and remain on the distal end 114 of the catheter 100. On deflation of the seamless balloon 210, these soft clots may travel distally and result in embolization of distal vessels—potentially resulting in additional procedural time or impact to patient health.

Figure 13B:
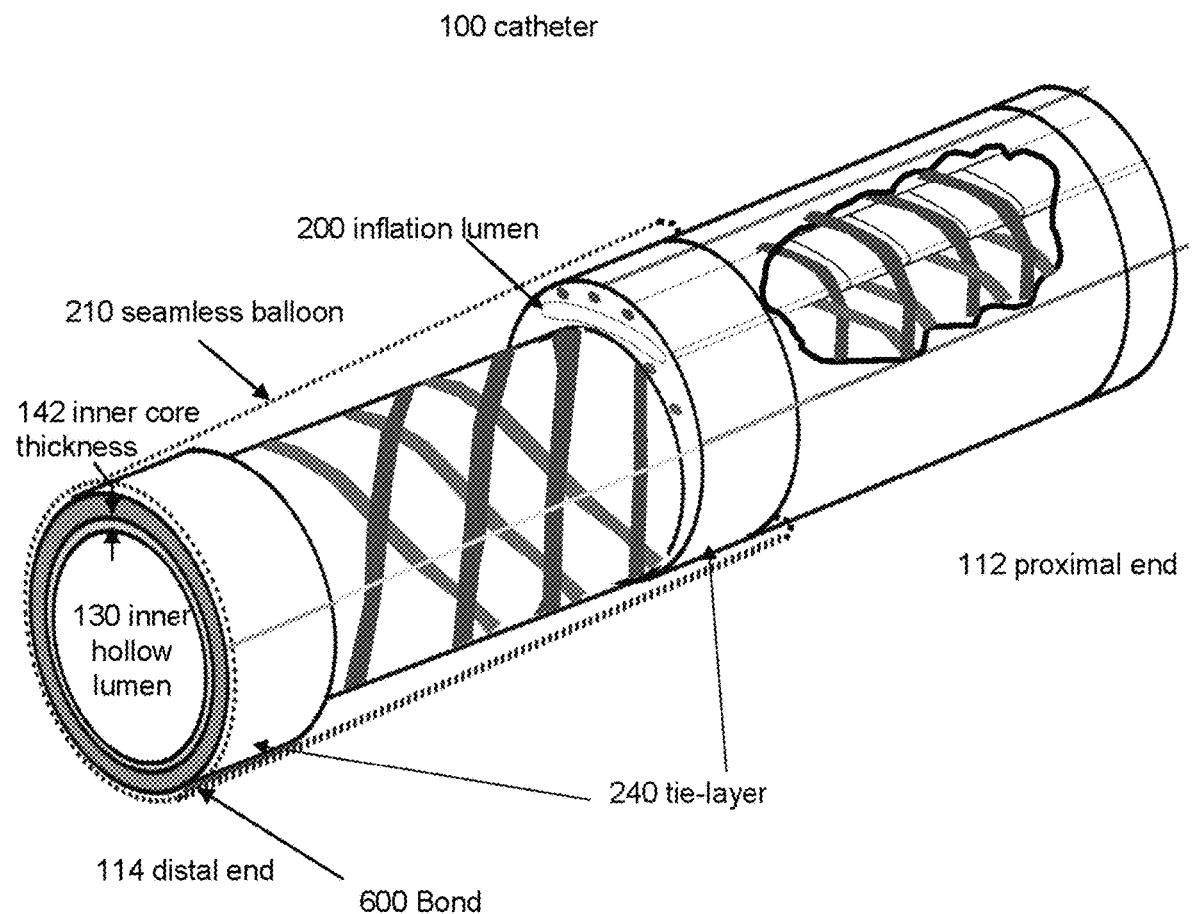
FIG. 13B is a top-front perspective illustration of the bonded, deflated seamless balloon of the present invention.

FIG. 13B illustrates a deflated, bonded 600 seamless balloon 210 profile and wire 300 wire configuration 400 of the catheter 100. The seamless balloon 210 can be secured to the elongated tubular member 110 by a tie-layer 240 and/or bond 600. The seamless balloon 210 can extend beyond the distal end 114 of the elongated tubular member 110. The seamless balloon 210 can be deflated as illustrated. The reinforcement of the wire configuration 400 by the wire 300 does not impede the deflation of the seamless balloon 210.

Figure 14A:
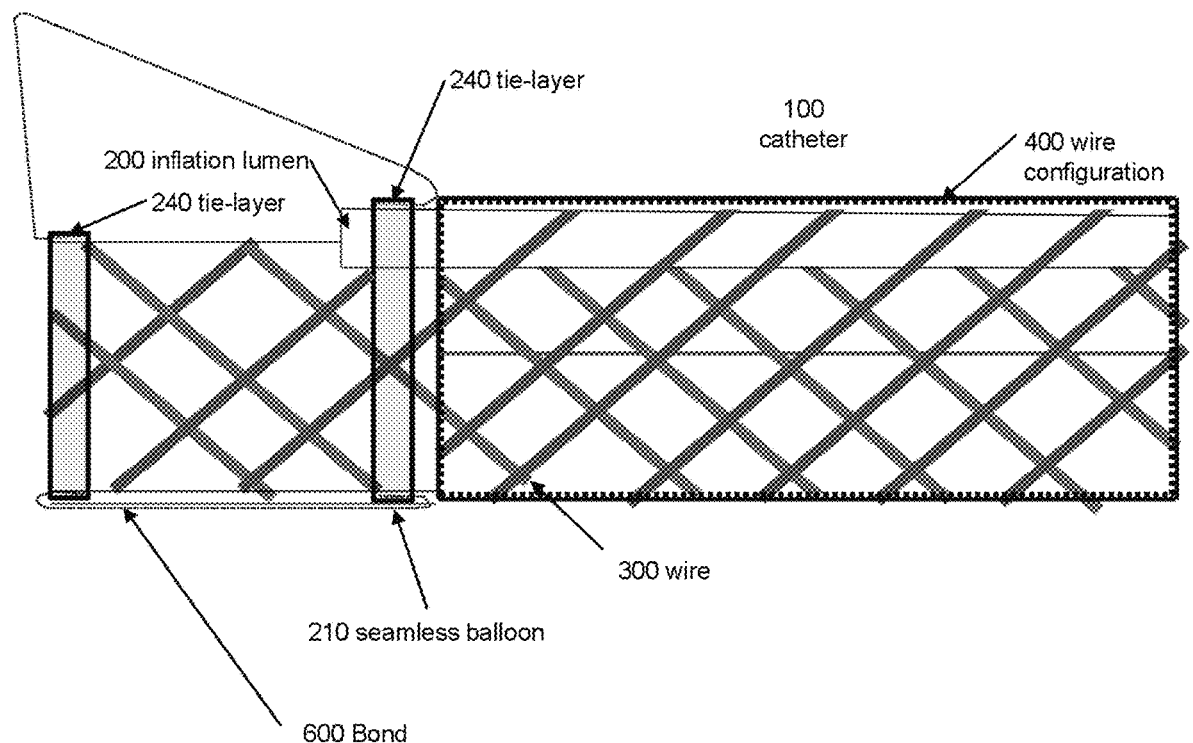
FIG. 14A is a side view illustration of the bonded, inflated seamless balloon of the present invention.

FIG. 14A illustrates an inflated, bonded 600 seamless balloon 210 profile and wire configuration 400 of the catheter 100. The seamless balloon 210 can be secured to the elongated tubular member 110 by a tie-layer 240 and/or bond 600, so that when inflated it does not inflate circumferentially. The seamless balloon 210 can extend beyond the distal end 114 of the elongated tubular member 110. The seamless balloon 210 can be inflated as illustrated. The reinforcement of the braided, wire configuration 400 by the wire 300 does not impede the inflation of the seamless balloon 210.

Figure 14B:
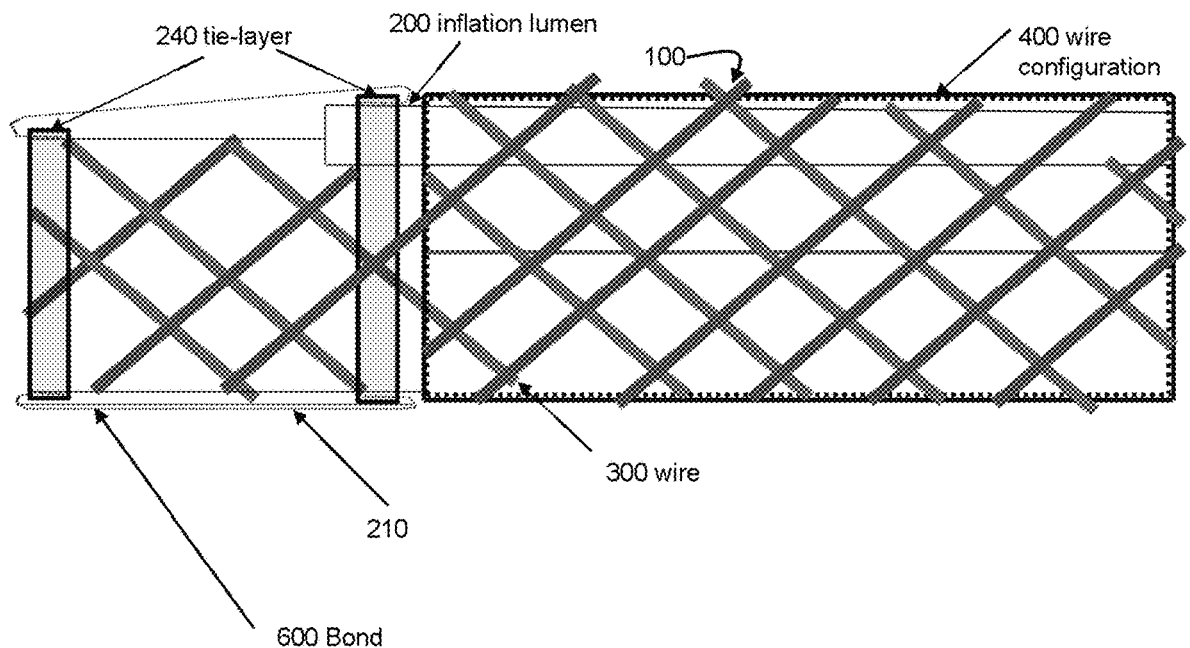
FIG. 14B is a side view illustration of bonded, deflated seamless balloon of the present invention.

FIG. 14B illustrates a deflated, bonded 600 seamless balloon 210 profile and wire configuration 400 of the catheter 100. The seamless balloon 210 can be secured to the elongated tubular member 110 by a tie-layer 240 and/or bond 600. The seamless balloon 210 can extend beyond the distal end 114 of the elongated tubular member 110. The seamless balloon 210 can be deflated as illustrated. The reinforcement of the braided and coil wire configuration 400 by the wire 300 does not impede the deflation of the seamless balloon 210.

The degree of eccentricity or inflation asymmetry can be altered by the placement of the bond 600. The seamless balloon 210 can be bonded 600 across either a small or large arc of the elongated tubular member 110. Also, eccentricity can be imposed by changing the inner core thickness 144 between the top and the bottom, making the inner hollow lumen 130 off center from a center axis of the catheter 100.

In most examples the seamless balloon 210 is inflated inside the patient's vascular using a saline or other neutral fluid. The fluid is pumped into the proximal end 112 of the inflation lumen 200 and fills the seamless balloon 210. The fluid volume and/or pressure is held constant to keep the balloon 210 engaged with the vascular lumen to prevent flow past the balloon 210. To deflate, the fluid is drawn out through the same lumen 200.

Figure 15A:
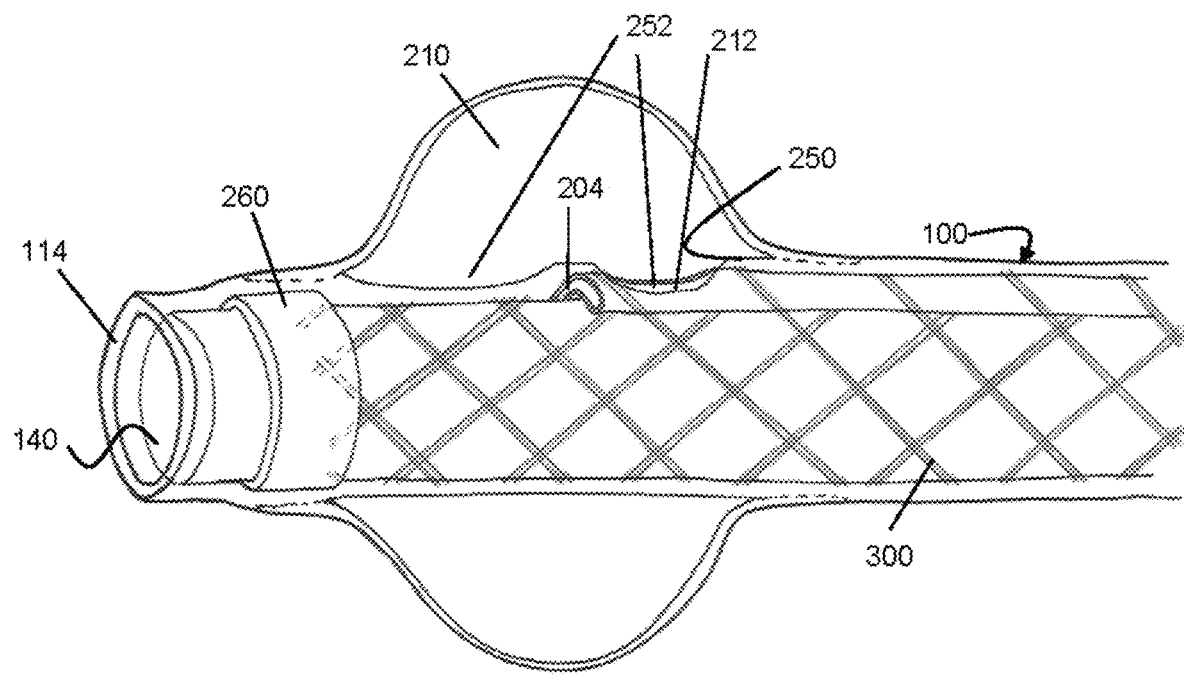
FIG. 15A is a side view illustration of a distal portion of an inflated balloon guide catheter of the present invention.

FIG. 15A illustrates a distal portion of a balloon guide catheter 100 of the present invention with an inflated balloon 210. The catheter 100 can include a tubular jacket 250 extending over wires 300. The tubular jacket 250 can extend over the distal portion of the balloon guide catheter 100, beyond the distal end 204 of the inflation lumen 200. The balloon 210 can be welded proximally and distally to an intermediate (or tie-layer) jacket material 250 formed from a blend of the balloon material and a soft urethane (such as Pellethane 80A). The jacket 250 can include openings 252 to allow a flow path between the inflation lumen 200 and the interior of the balloon 210.

The distal tip 114 of the catheter 100 can be formed from this intermediate (or tie-layer) material, or from the balloon material itself, or form another soft material compatible with the intermediate (or tie-layer) material.

The distal tip material can extend slightly beyond the inner PTFE liner, inner core 140 of the main catheter lumen 130, creating a very soft tip that can flare to accept soft clot with minimal risk of shear. A radiopaque marker band 260 can be positioned just proximal of the distal end 114 of the catheter 100, and the catheter reinforcing braid 300 can terminate beneath this marker 260 to minimize the risk of exposed braid wires 300. The inflation lumen 200 can terminate under the balloon 210 and a skive or cut-away 212 can be added to allow the lumen of the inflation lumen 200 to communicate with the interior of the balloon 210 to allow inflation/deflation.

The stiffness of this catheter 100 can increase gradually from distal to proximal. The stiffness gradient can be primarily created by the modulus of the different segments of polymer jacket material 250. Polymer jacket material 250 can be laminated onto the catheter 100 over the braid 300 and inflation lumen 200. This lamination process ideally melts the jacket material sufficiently to allow it to flow beneath the inflation lumen and integrate to the strike layers of the inflation lumen and of the PTFE liner of the main catheter lumen.

Figure 15B:
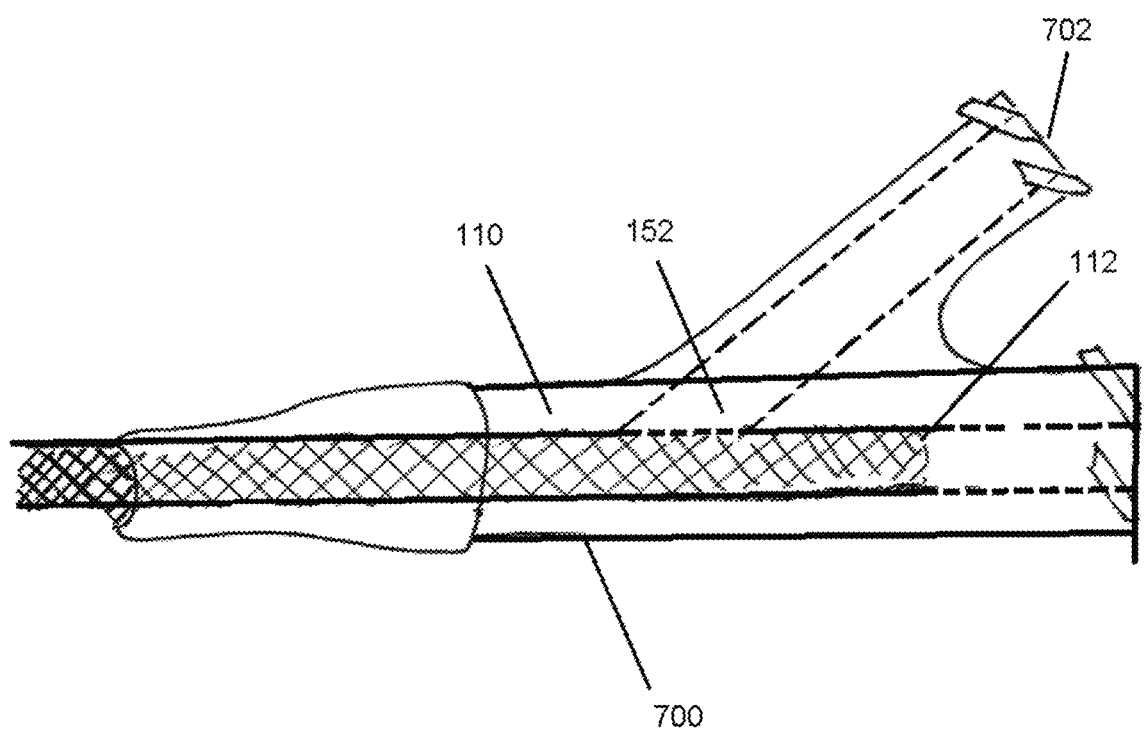
FIG. 15B is a side view illustration of a proximal portion of a balloon guide catheter of the present invention inserted in a proximal luer.

FIG. 15B illustrates a proximal portion of a balloon guide 100 of the invention inserted in a proximal luer 700. A skive or cut-away 152 in the outer jacket 250, wires 300, and inflation lumen 200 can provide a flow path through the inflation lumen 200 to an angled port 702 of the proximal luer 700 and thus to facilitate control of balloon inflation/deflation through this port 702.

FIGS. 16A-D illustrate various alternative inflation lumen configurations using multiple inflation lumens 200a, 200b, 200c, 200d. The inner hollow lumens 130a, 130b, 130c, 130d of each elongated tubular member 110a, 110b, 110c, 110d is identified in each respective figure to orient the reader.

Catheters having multiple inflation lumens can aid in preparation of the catheter and facilitate expedited inflation and deflation of a balloon. During preparation, one or more inflation lumens can receive an injection of 50/50 contrast mix to inflate the balloon and one or more different inflation lumens can be used as a vent or exhaust for any air in the system and the contrast mixture. In a catheter having dual inflation lumens, therefore, contrast mixture would enter a first of the inflation lumens, travel distally along the elongated tubular member, enter the balloon, enter a second of the inflation lumens at its distal end, travel proximally along the elongated tubular member, and exit the catheter form the second inflation lumen. An inflation lumen that is used for venting (e.g. the second inflation lumen in the dual lumen catheter in the previous example) can also be referred to as a venting lumen. Utilizing an inflation lumen and a vent lumen as described can purge air from the inflation lumen, vent lumen, and balloon during preparation. During a procedure, all lumens can be used in parallel to simultaneously inflate or simultaneously deflate. Multiple inflation lumens can therefore facilitate faster inflation and deflation of the balloon compare to single lumen catheters. Multiple inflation lumens can also provide redundancy; in the case that one inflation lumen is kinked, blocked, otherwise compromised, in some applications the remaining operable inflation lumen or lumens can provide sufficient flow to and from the balloon to inflate and/or deflate the balloon.

FIG. 16A illustrates a cross section of an elongated tubular member 110a having dual inflation lumens 200a with a wire pattern in which the reinforcing wires 300a run over and under both inflation lumens 200a together.

FIG. 16B illustrates a cross section of an elongated tubular member 110b having dual inflation lumens 200b with a wire pattern in which the reinforcing wires 300b run over and under each inflation lumen 200b individually. Configured as illustrated in FIG. 16B, the wires 300b can separate the inflation lumens 200b such that the inflation lumens 200b are inhibited from shifting to overlap as the elongated tubular member 110b flexes.

FIG. 16C illustrates a cross section of an elongated tubular member 110c having three inflation lumens 200c. Although not illustrated, other variants with more than 3 inflation lumens are also envisaged.

FIG. 16D illustrates a cross section of an elongated tubular member 110d having dual inflation lumens 200d positioned on opposite sides of the circumference of the elongated tubular member 110d, offset approximately 180 degrees apart.

Figures 17A, 17B:
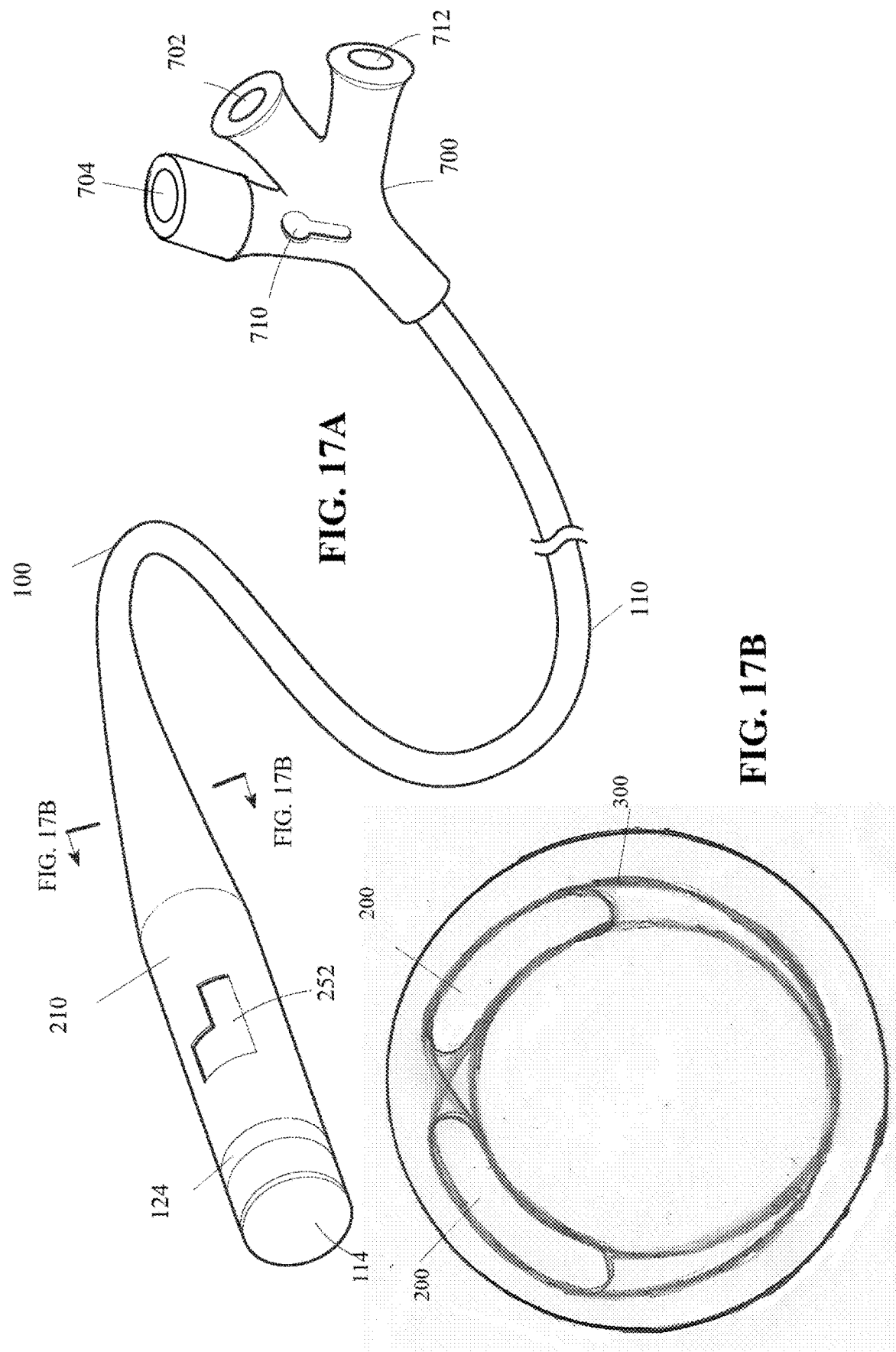
FIG. 17A is a perspective view illustration of a dual inflation lumen catheter and proximal luer of the present invention.
FIG. 17B is a cross section illustration of an elongated tubular member of the present invention.

FIG. 17A illustrates a dual inflation lumen catheter 100 connected to a proximal luer 700 configured to flush, inflate, and deflate a balloon. FIG. 17B illustrates a cross section of an elongated tubular member 110 that can be used as the elongated tubular member 110 illustrated in FIG. 17A. A person of ordinary skill in the art would appreciate and understand that a dual inflation lumen catheter having an alternative configuration can be used as the catheter 100 illustrated in FIG. 17A. For example, a catheter having an elongated tubular member 110a, 110b, 110d as illustrated in FIGS. 16A, 16B, and 16D are suitable.

Referring collectively to FIG. 17A and 17B, the catheter 100 can include an inflation port 252 positioned under the balloon that is an opening in the elongated tubular member 110d that provides a flow path from one or both of the inflation lumens 200 into the balloon 210. The catheter 100 can include two inflation ports 252, one for each inflation lumen 200 in the dual inflation lumen catheter 100.

The proximal luer 700 can include two inflation lumen ports 702, 704 that can be used to provide fluid for flushing and inflating the inflation lumens and balloons and that can be used to provide suction to deflate the balloon. The proximal luer 700 can include a valve 710 that can be moved to isolate the inflation lumens from each other within the proximal luer 700 or to provide a flow path between the two inflation lumens within the proximal luer 700.

Figure 18A:
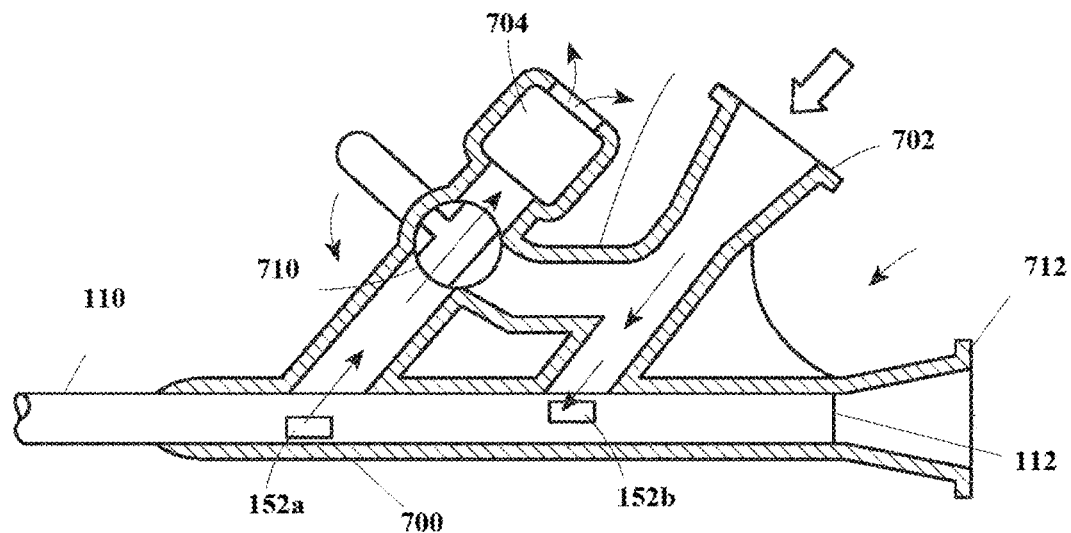
FIG. 18A is a cross section illustration of a proximal luer of the present invention configured to flush a balloon and inflation lumens.
Figure 18B:
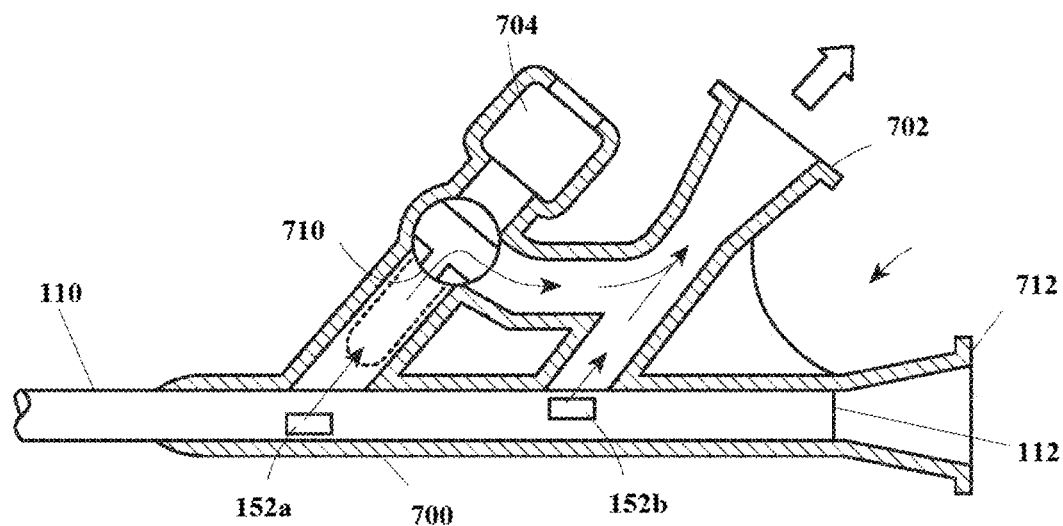
FIG. 18B is a cross section illustration of a proximal luer of the present invention configured to deflate the balloon simultaneously through dual lumens.

FIGS. 18A and 18B illustrate cross sectional views of a proximal luer 700 that can receive an elongated tubular member 110, 110a, 110b, 110d having dual inflation lumens 200, 200a, 200b, 200d. FIG. 18A illustrates the proximal luer 700 with the valve 710 in an isolation position such that the two inflation lumens are isolated from each other within the proximal luer 700. FIG. 18B illustrates the proximal luer 700 with the valve 710 in a communication position such that the two inflation lumens are in communication with each other within the proximal luer 700.

Referring to FIG. 18A, when the valve 710 is in the isolation position, the proximal luer 700 can be used to flush the inflation lumens and balloon. Fluid such as a 50/50 contrast mix can be injected into a first port 702, flow through the port into a cut-away 152b in the elongated tubular member 110 providing a fluidic flow into one of the inflation lumens. Fluid can be flowed through the system as indicated by the arrows. The injected fluid can flow distally through the elongated tubular member 110, through an inflation port 252 under the balloon 210, into the balloon 210, back into an inflation port 252 under the balloon, proximally through the elongated tubular member 110, out a second cut-away 152a in the elongated tubular member 110, into the proximal luer 700, through an opening in the valve 710, and out a second port 704 in the proximal luer. The proximal luer 700 can also include a proximal opening 712 through which devices can be delivered into the proximal end 112 of the elongated tubular member 110 and through the inner lumen 130 of the elongated tubular member 110.

The luer 700 can also include a filter that allows air flow but is impervious to liquid that is in communication with the second port 704 such that fluid flowed into the first port 702 can fill the inflation lumens and balloon with fluid and purge the inflation lumens and balloon of air.

Referring to FIG. 18B, when the valve 710 is in the communication position, the proximal luer 700 can be used to inflate or deflate the balloon simultaneously through both inflation lumens of the dual lumen catheter. FIG. 18B illustrates fluid flow during deflation as indicated by the arrows. For inflation, fluid flow is in the opposite direction as indicated by the arrows. In the communication position, the second port 704 in the proximal luer 700 can be blocked and a channel connecting the two inflation lumens can be unblocked. To deflate, a vacuum can be applied to the first port 702 of the proximal luer 700. Vacuum can be translated through the proximal luer 700 as indicated by the arrows and withdraw fluid from the dual lumens via each cut-away 152a, 152b in the elongated tubular member 110. The vacuum can be translated through both inflation lumens to the balloon, thereby extracting fluid from the balloon via both inflation lumens simultaneously. For inflation, a pressurized fluid source can be provided at the first port 702 of the proximal luer 700 and fluid flow is in the opposite direction as described.

The descriptions contained herein are examples of embodiments of the invention and are not intended in any way to limit the scope of the invention. As described herein, the invention contemplates many variations and modifications of the device. These modifications would be apparent to those having ordinary skill in the art to which this invention relates and are intended to be within the scope of the claims which follow.

What is claimed is:

1. A catheter comprising:
    an elongated tubular member comprising:
        a proximal end;
        a distal end;
        a top;
        a bottom; and
        an outer surface;
        two inner surfaces comprising:
            an inner hollow lumen extending between the proximal end and the distal end;
            an inflation lumen extending between the proximal end and the distal end; the inflation lumen is disposed radially outward of the inner hollow lumen;
        wherein the inflation lumen is smaller than the inner hollow lumen;
        wherein the inflation lumen is located approximate at least one of the top or bottom portion of the elongated tubular member outside the inner hollow lumen;
        an inner core with an inner core thickness and forming the inner hollow lumen;
        a balloon connected to the inflation lumen;
        wherein the balloon extends from the distal end and secured to the elongated tubular member;
        a wire configuration pattern comprising a wire that segregates the wire over the inflation lumen securing the inflation lumen exteriorly to the inner core; the wire being arranged exteriorly of the inner hollow lumen and exteriorly of the inflation lumen .
2. The catheter of claim 1, wherein the balloon extends beyond the distal end of the elongated tubular member.
3. The catheter of claim 1, wherein the balloon is secured to the elongated tubular member by a tie-layer.
4. The catheter of claim 1, wherein the wire configuration comprises a braided pattern.
5. The catheter of claim 1, further comprising a split wire configuration comprising a wire that segregates the wire both under and over the inflation lumen.
6. The catheter of claim 5, wherein the wire configuration comprises a braided pattern.
7. A catheter comprising:
    an elongated tubular member comprising:
        a proximal end;
        a distal end;
        a top;
        a bottom; and
        an outer surface;
        two inner surfaces comprising:
            an inner hollow lumen extending between the proximal end and the distal end;
            an inflation lumen extending between the proximal end and the distal end;
            wherein the inflation lumen is smaller than the inner hollow lumen;
            wherein the inflation lumen is located approximate at least one of the top or bottom portion of the elongated tubular member outside the inner hollow lumen;
        an inner core with an inner core thickness;
        a balloon connected to the inflation lumen;
            wherein the balloon extends from the distal end and secured to the elongated tubular member;
        wherein a seamless balloon is secured to the elongated tubular member by a bond across only a partial arc of the elongated tube member ensuring that the seamless balloon inflates eccentrically.
8. The catheter of claim 7, wherein when inflated the balloon is not concentric with the inner core.
9. The catheter of claim 7, wherein a degree of eccentricity in which the seamless balloon inflates eccentrically is altered by placement of the bond.
10. A catheter comprising:
    a substantially tubular inner core forming an inner hollow lumen;
    a first inflation sleeve comprising a first inflation lumen therethrough and extending a majority of the length of the tubular inner core;
    a wound wire mesh securing the first inflation sleeve to an outer surface of the tubular inner core; wherein the wound wire mesh secures a second inflation sleeve to the outer surface of the tubular inner core;
    a balloon affixed to a distal portion of the tubular inner core and in fluidic communication with the first inflation lumen of the first inflation sleeve.
11. The catheter of claim 10, wherein the first inflation sleeve comprises a substantially crescent shape cross section.
12. The catheter of claim 10, further comprising a polymeric layer disposed between the first inflation sleeve and the wound wire mesh.
13. The catheter of claim 12, further comprising a polymeric jacket sleeve encircling the tubular inner core.
14. The catheter of claim 13, wherein the polymeric jacket sleeve is fused with the polymeric layer disposed between the inflation sleeve and the wound wire mesh, and wherein the polymeric jacket sleeve effectively seals a damaged opening in the first inflation sleeve.

15. The catheter of claim 7, wherein the wound wire mesh comprises wires that run together over and under the first inflation sleeve and the second inflation sleeve collectively.

16. The catheter of claim 10, wherein the wound wire mesh comprises wires that run individually over and under the first inflation sleeve and the second inflation sleeve thereby separating the first inflation sleeve from the second inflation sleeve.

17. The catheter of claim 10, wherein the balloon inflates to have a substantially trapezoidal profile characterized by a larger diameter distal end and a smaller diameter proximal end.

18. The catheter of claim 17, wherein the balloon inflates to define an angle measurable between a line parallel to a non-parallel side of the trapezoidal profile and a line parallel to the distal portion of the tubular inner core, and wherein the angle measures less than 70 degrees.

19. The catheter of claim 10, wherein the wound wire mesh comprises:
 a first plurality of wire segments extending across an outer surface of the first inflation sleeve; and
 a second plurality of wire segments extending under an inner surface of the first inflation sleeve,
 wherein a majority of the wire segments in the first plurality of wire segments are each substantially parallel to each other,
 wherein a majority of the wire segments in the second plurality of wire segments are each substantially parallel to each other, and
 wherein some of the first plurality of wire segments cross some of the second plurality of wire segments.

20. An assembly comprising:
 a catheter comprising:
  a substantially tubular inner core forming an inner hollow lumen;
  a first inflation sleeve comprising a first inflation lumen therethrough and extending a majority of the length of the tubular inner core;
  a wound wire mesh securing the first inflation sleeve to an outer surface of the tubular inner core;
  a balloon affixed to a distal portion of the tubular inner core and in fluidic communication with the first inflation lumen of the first inflation sleeve;
  a second inflation sleeve comprising a second inflation lumen therethrough and extending a majority of the length of the tubular inner core; wherein the wound wire mesh secures the second inflation sleeve to the outer surface of the tubular inner core;
  a first opening approximate a proximal end of the catheter providing a first fluidic passageway from the first inflation lumen of the first inflation sleeve to exterior of the catheter; and
  a second opening approximate the proximal end of the catheter providing a second fluidic passageway from the second inflation lumen of the second inflation sleeve to the exterior of the catheter; and
 a luer comprising:
  a distal opening sized to receive a proximal portion of the catheter;
  a vent port configured to communicate with the second opening;
  a pump port configured to communicate with the first opening; and
  a proximal opening configured to allow insertion of devices into an inner hollow lumen of the catheter.

21. The assembly of claim 20, wherein the luer further comprises:
 a valve movable from an isolation position to a communication position, wherein, when the valve is in the isolation position, the luer is configured to isolate flow to or from the second opening from flow to or from the first opening, and wherein, when the valve is in the communication position, the luer is configured to provide a fluid path between the second opening and the first opening.

22. A method for operating an assembly including: a catheter having: a substantially tubular inner core forming an inner hollow lumen; a first inflation sleeve comprising a first inflation lumen therethrough and extending a majority of the length of the tubular inner core; a wound wire mesh securing the first inflation sleeve to an outer surface of the tubular inner core; a balloon affixed to a distal portion of the tubular inner core and in fluidic communication with the first inflation lumen of the first inflation sleeve; a second inflation sleeve comprising a second inflation lumen therethrough and extending a majority of the length of the tubular inner core, wherein the wound wire mesh secures the second inflation sleeve to the outer surface of the tubular inner core; a first opening approximate a proximal end of the catheter providing a first fluidic passageway from the first inflation lumen of the first inflation sleeve to exterior of the catheter; and a second opening approximate the proximal end of the catheter providing a second fluidic passageway from the second inflation lumen of the second inflation sleeve to the exterior of the catheter; and the assembly further including a luer having: a distal opening sized to receive a proximal portion of the catheter; a vent port configured to communicate with the second opening; a pump port configured to communicate with the first opening; and a proximal opening configured to allow insertion of devices into an inner hollow lumen of the catheter, the method comprising the step of:
 flowing a fluid into and out of the catheter by flowing the fluid into the first inflation lumen, through the balloon, and out the second inflation lumen.

23. The method of claim 22, further comprising the step of:
 inflating the balloon by providing the fluid simultaneously into the first inflation lumen and the second inflation lumen.

24. The method of claim 22, further comprising the step of:
 deflating the balloon by providing suction simultaneously at the first inflation lumen and the second inflation lumen.

* * * * *